US010759749B2

(12) United States Patent
Seino et al.

(10) Patent No.: US 10,759,749 B2
(45) Date of Patent: Sep. 1, 2020

(54) THERAPEUTIC AGENT FOR DIABETES

(71) Applicants: JCR Pharmaceuticals Co., Ltd., Ashiya-shi (JP); National University Corporation Kobe University, Kobe-shi (JP); National University Corporation Chiba University, Chiba-shi (JP)

(72) Inventors: Susumu Seino, Kobe (JP); Kenji Sugawara, Kobe (JP); Ichiro Mori, Kobe (JP); Akio Matsumoto, Chiba (JP); Yoshie Reien, Chiba (JP)

(73) Assignees: JCR Pharmaceuticals Co., Ltd., Ashiya-shi (JP); National University Corporation Kone University, Kobe-shi (JP); National University Corporation Chiba University, Chiba-shi (JP)

( * ) Notice: Subject to any disclaimer, the term of this patent is extended or adjusted under 35 U.S.C. 154(b) by 0 days.

(21) Appl. No.: 16/329,025

(22) PCT Filed: Aug. 28, 2017

(86) PCT No.: PCT/JP2017/030738
§ 371 (c)(1),
(2) Date: Feb. 27, 2019

(87) PCT Pub. No.: WO2018/043399
PCT Pub. Date: Mar. 8, 2018

(65) Prior Publication Data
US 2019/0202781 A1 Jul. 4, 2019

(30) Foreign Application Priority Data
Aug. 31, 2016 (JP) ................. 2016-170346

(51) Int. Cl.
| | | |
|---|---|---|
| *C07D 337/06* | (2006.01) | |
| *C07C 337/06* | (2006.01) | |
| *C07C 281/06* | (2006.01) | |
| *A61P 3/10* | (2006.01) | |
| *A61K 31/17* | (2006.01) | |
| *A61K 31/175* | (2006.01) | |
| *A61P 3/08* | (2006.01) | |
| *A61K 9/00* | (2006.01) | |

(52) U.S. Cl.
CPC .......... *C07C 337/06* (2013.01); *A61K 9/0053* (2013.01); *A61K 31/17* (2013.01); *A61K 31/175* (2013.01); *A61P 3/08* (2018.01); *A61P 3/10* (2018.01); *C07C 281/06* (2013.01)

(58) Field of Classification Search
CPC ................. C07C 337/06; A61P 3/08
See application file for complete search history.

(56) References Cited

U.S. PATENT DOCUMENTS

| 8,642,660 B2 * | 2/2014 | Goldfarb .............. A61K 31/122 514/641 |
|---|---|---|
| 2004/0087659 A1 | 5/2004 | Defossa et al. |
| 2006/0205772 A1 | 9/2006 | Coppola et al. |
| 2007/0155803 A1 | 7/2007 | Bondebjerg et al. |

FOREIGN PATENT DOCUMENTS

| JP | 2003-211840 A | 7/2003 |
|---|---|---|
| JP | 2005-532402 A | 10/2005 |
| JP | 2006-517199 A | 7/2006 |
| WO | WO 2004/007437 A1 | 1/2004 |
| WO | WO 2004/065351 A1 | 8/2004 |
| WO | WO 2010/119693 A1 | 10/2010 |

OTHER PUBLICATIONS

Goldfarb et al (2009): STN International (Columbus, Ohio), HCAPLUS database, Accession No. 2009: 846113.*
Scott et al (1958): STN International (Columbus, Ohio), HCAPLUS database, Accession No. 1958: 34908.*
International Search Report dated Sep. 26, 2017 in PCT/JP2017/030738, citing documents AP, AQ, AS, AAK, AAM-AAO therein, 2 pages.
International Preliminary Report on Patentability and Written Opinion dated Mar. 5, 2019 in PCT/JP2017/030738 (with English Translation), citing documents AP, AQ, AS, AAK, AAM-AAO therein, 10 pages.
Stephanie Aleskow Stein et al., "A Review of the Efficacy and Safety of Oral Antidiabetic Drugs", Expert. Opin. Drug. Saf., 12, 2013, pp. 1-35.
Nobuya Inagaki et al., "Reconstitution of /KATP: An Inward Rectifier Subunit Plus the Sulfonylurea Receptor", Science, vol. 270, Nov. 17, 1995, pp. 1166-1170.
Hiroshi Sakura et al., "Characterization and Variation of a Human Inwardly-rectifying K-channel Gene (KCNJ6): a Putative ATP-sensitive K-channel Subunit", FEBS letters, 367, 1995, pp. 193-197.
Susumu Seino, "ATP-Sensitive Potassium Channels: A Model of Heteromultimeric Potassium Channel/Receptor Assemblies", Annu. Rev. Physiol., vol. 61., 1999, pp. 337-362 and Cover Pages.
Frances M. Ashcroft et al., "Electrophysiology of the Pancreatic β-Cell", Prog. Biophys. Mol. Biol., vol. 54, 1999, pp. 87-143.
Lidia Aguilar-Bryan et al., "Molecular Biology of Adenosine Triphosphate-Sensitive Potassium Channels", Endocrine Rev., 20, 1999, pp. 101-135.

(Continued)

Primary Examiner — Golam M Shameem
(74) Attorney, Agent, or Firm — Oblon, McClelland, Maier & Neustadt, L.L.P.

(57) ABSTRACT

A nobel therapeutic agent for diabetes which can suppress occurrence of side effects such as persistent hypoglycemia is provided. The active ingredient is a derivative of 1,1-diphenylsemicarbazide or 1,1-diphenylthiosemicarbazide. In particular, the active ingredient is a derivative of 1,1-diphenyl-4-cyclohexyl-semicarbazide or 1,1-diphenyl-4-cyclohexyl-thiosemicarbazide exhibiting hypoglycemic action when orally administered.

12 Claims, 7 Drawing Sheets

(56) References Cited

OTHER PUBLICATIONS

Jean-Claude Henquin, "Triggering and Amplifying Pathways of Regulation of Insulin Secretion by Glucose", Diabetes, vol. 49, 2000, pp. 1751-1760.
Susumu Seino et al., "Physiological and pathophysiological roles of ATP-sensitive K + channels", Progress in Biophysics & Molecular Biology, 81, XP 2344317, 2003, pp. 133-176.
Chang-Liang Zhang et al., "The cAMP Sensor Epac2 Is a Direct Target of Antidiabetic Sulfonylurea Drugs", Science, vol. 325, 2009, pp. 607-610.
Toshimasa Takahashi et al., "Antidiabetic Sulfonylureas and cAMP Cooperatively Activate Epac2A", Sci. Signal., vol. 6, Issue 298 Ra94, 2013, pp. 1-9.
Harumi Takahashi et al., "Role of Epac2A/Rap1 Signaling in Interplay Between Incretin and Sulfonylurea in Insulin Secretion", Diabetes, vol. 64, 2015, pp. 1262-1272.
Ebenezer A. Nyenwe et al., "Management of Type 2 diabetes: Evolving Strategies for the Treatment of Patients with Type 2 Diabetes", Metabolism., 60.1-23(2011), pp. 1-44.
F. L. Scott et al.,"Polynitrogen Systems from the Hydrazinocarbonic Acids. V.[1] Aminolytic Reactions of N ,N-Diphenylcarbamyl Azide[2]", J. Am. Chem. Soc., vol. 79, 1957, pp. 6077-6082.
Ch. C. P. Pacilly, "The Action of Aliphatic Isocyanates on Hydrazine Derivatives", Recl. trav. chim. Pays-Bas.55., 1936, pp. 101-121.
Resistry(STN) [online]CAS registry No. 455309-99-6, 1 page, published Sep. 26, 2002.
Resistry(STN) [online]CAS registry No. 106437-84-7, 1 page, published Feb. 7, 1987.
Resistry(STN) [online]CAS registry No. 502969-01-9, 1 page, published Apr. 15, 2003.
Resistry(STN) [online]CAS registry No. 903805-03-8, Chemical Library, XP-002797889, Aug. 23, 2006, 1 pages.
K K.Ginwala, et al. Ynthesis of 1, 1-Diphenyl-4-Substituted Thiosemicarbazides Current Science, Letter of the Editor, XP 55670845, 1963, pp. 159-160.

* cited by examiner

[Figure 1]
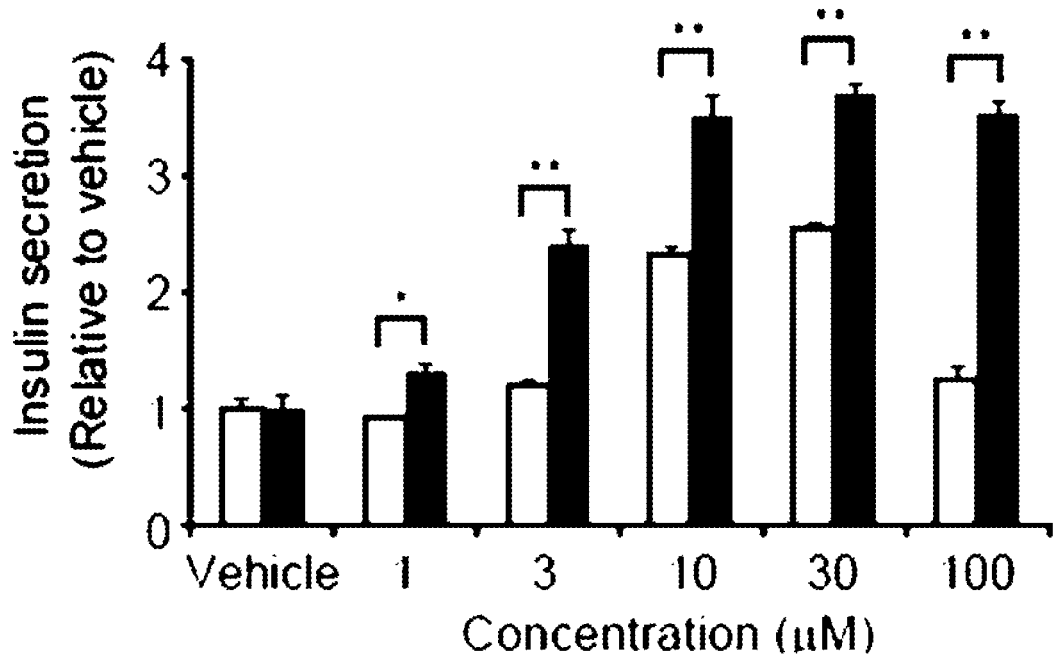
[Figure 2]
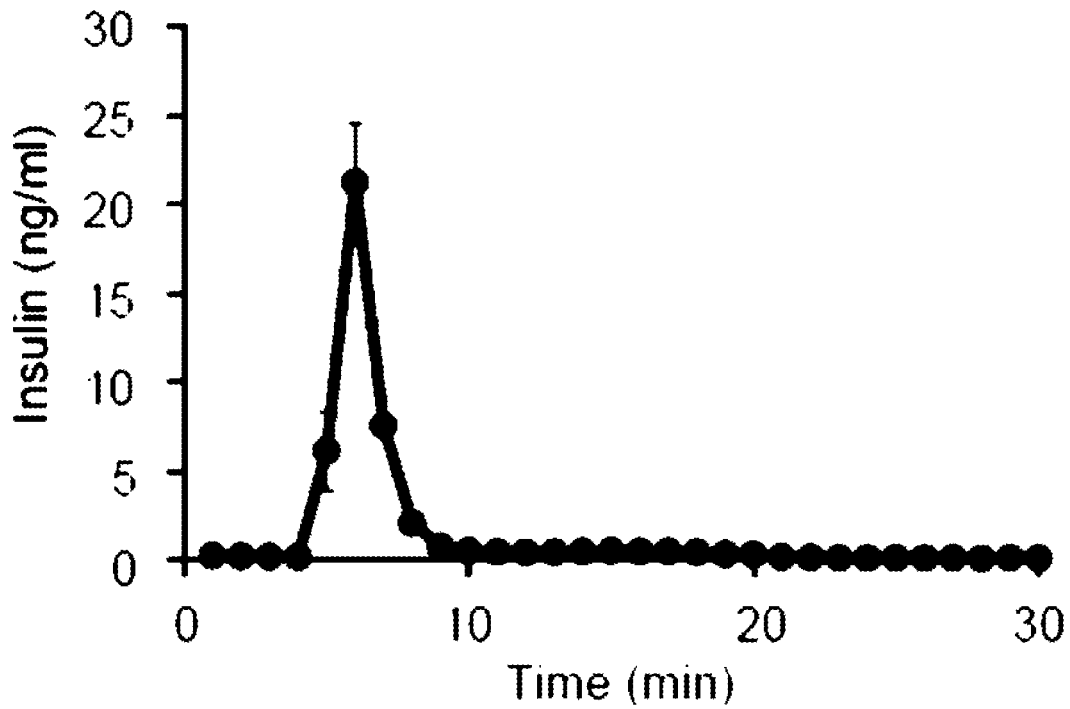

[Figure 3]
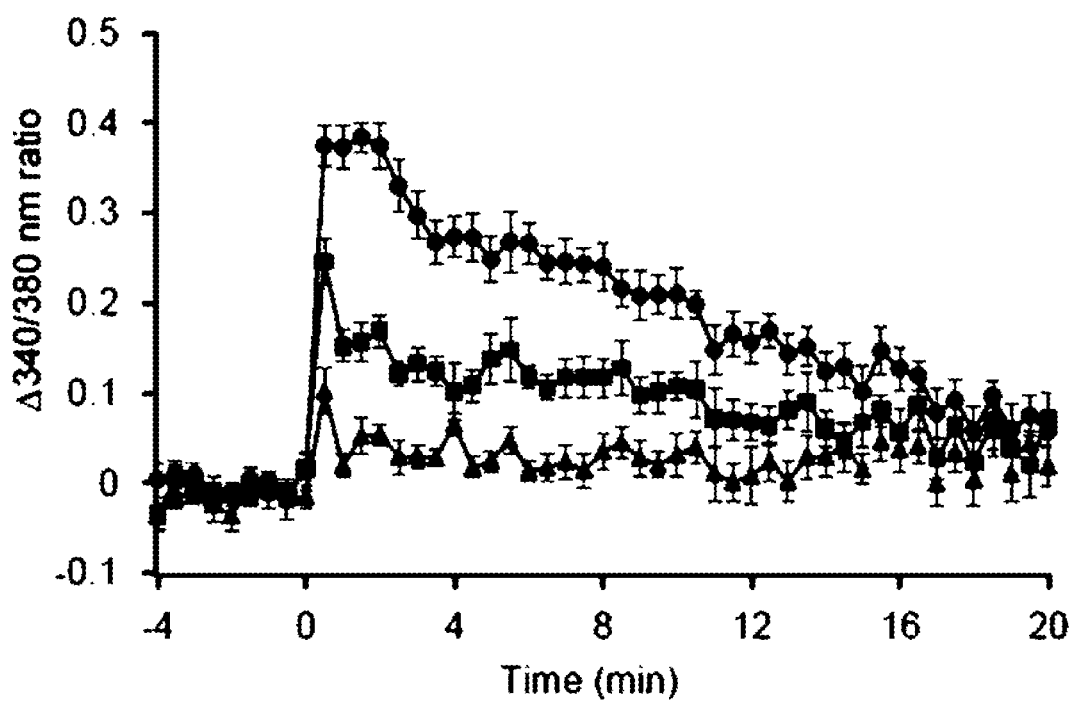

[Figure 4]
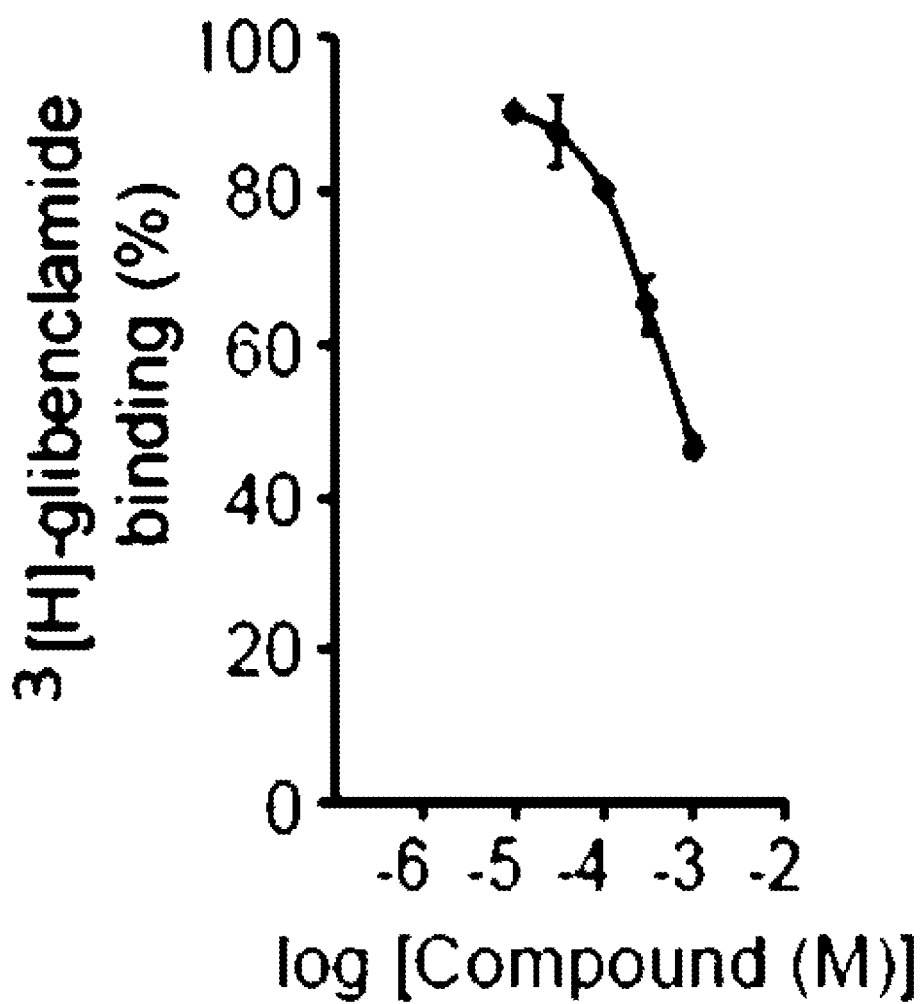

[Figure 5]
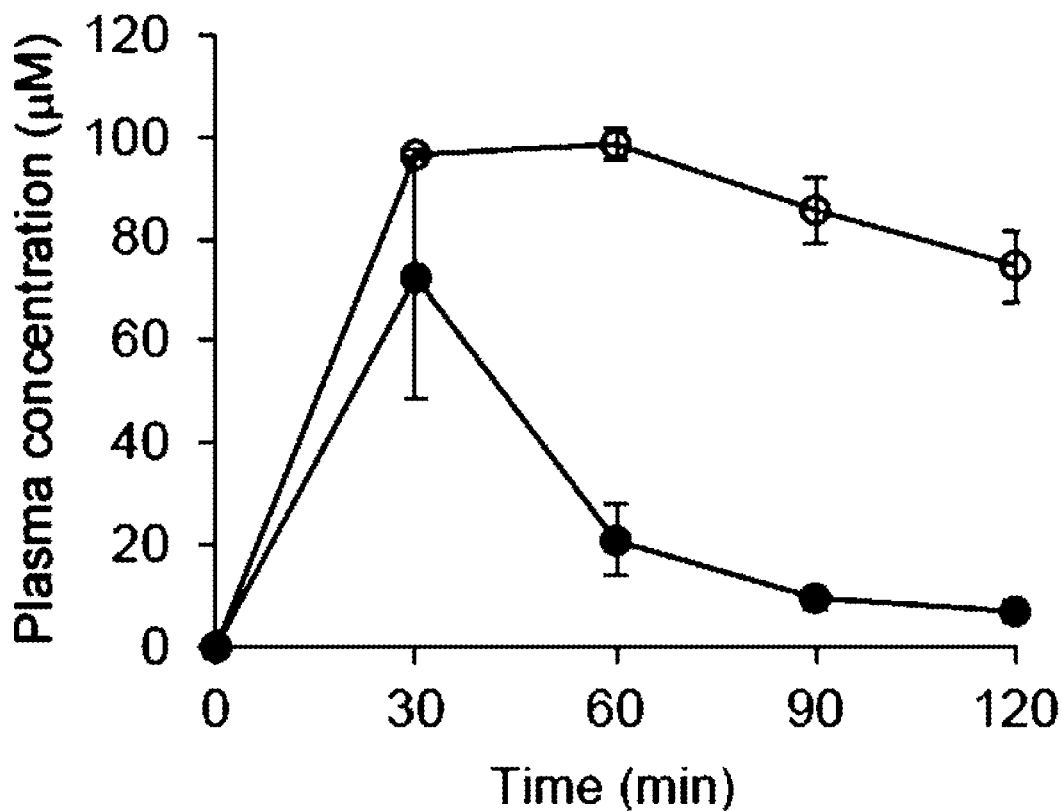
[Figure 6]
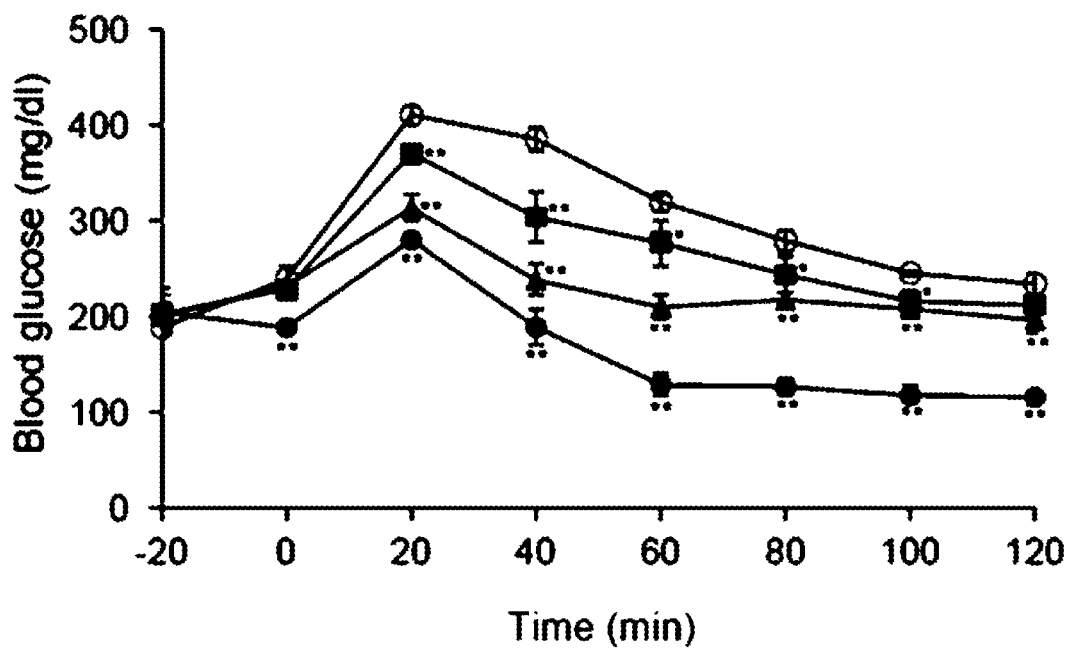

[Figure 7]
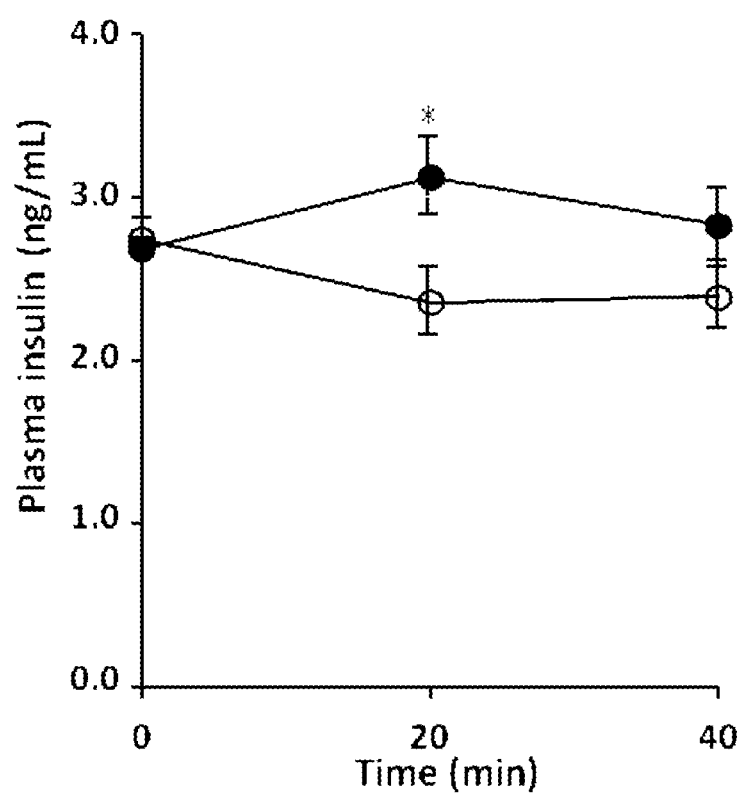

[Figure 8]
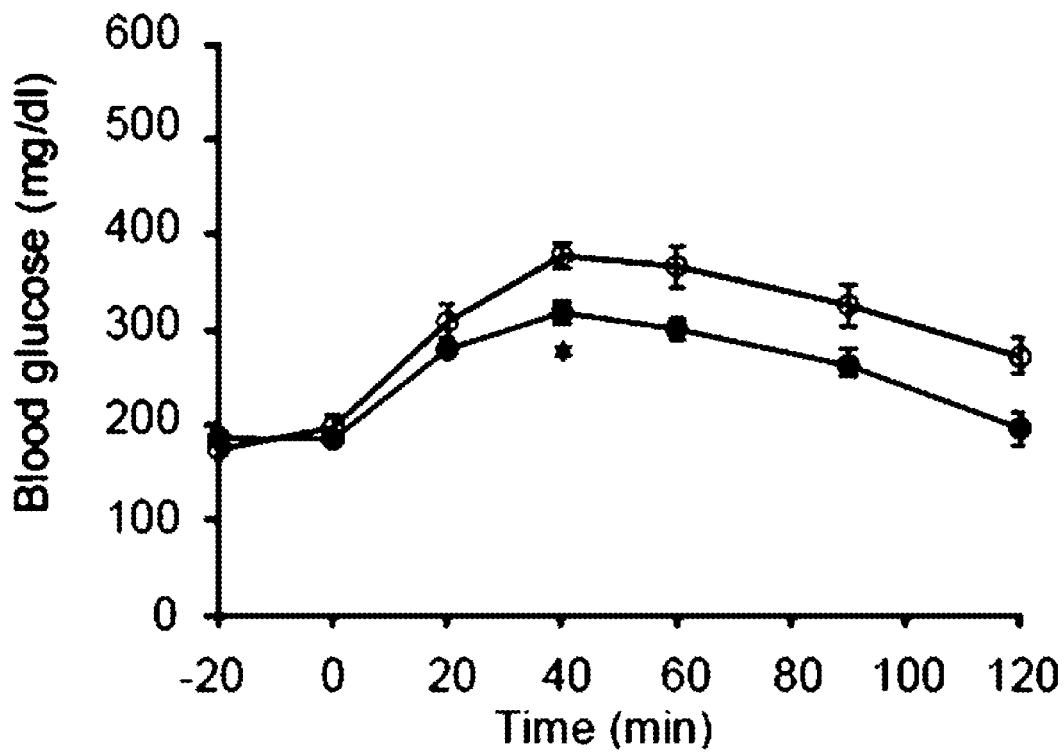
[Figure 9]
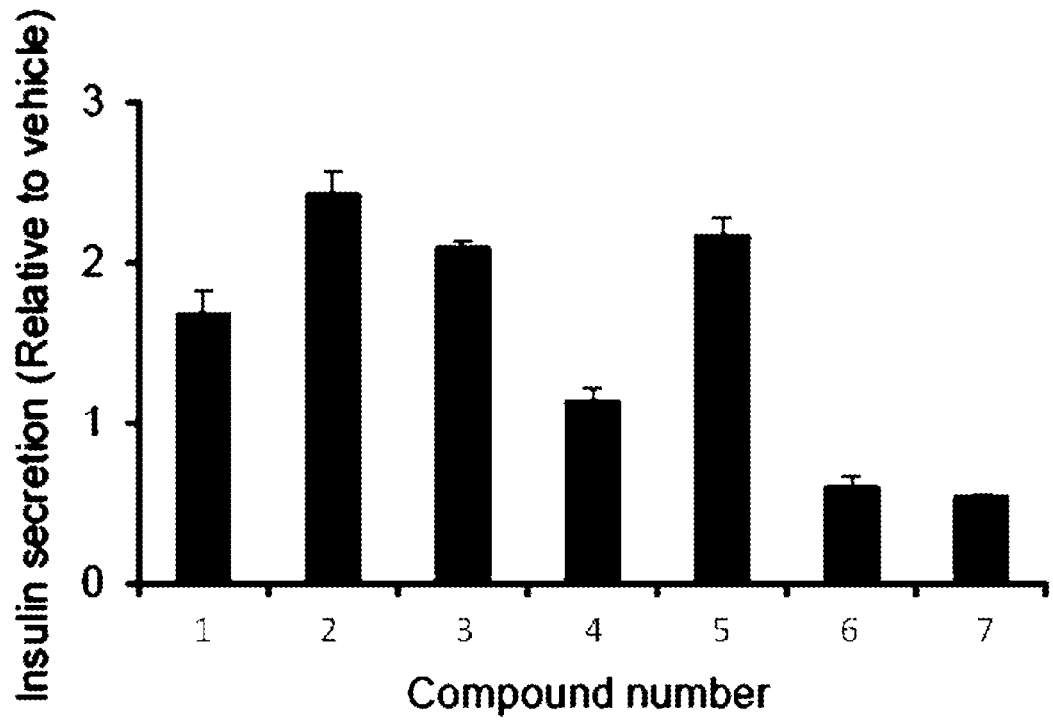

[Figure 10]
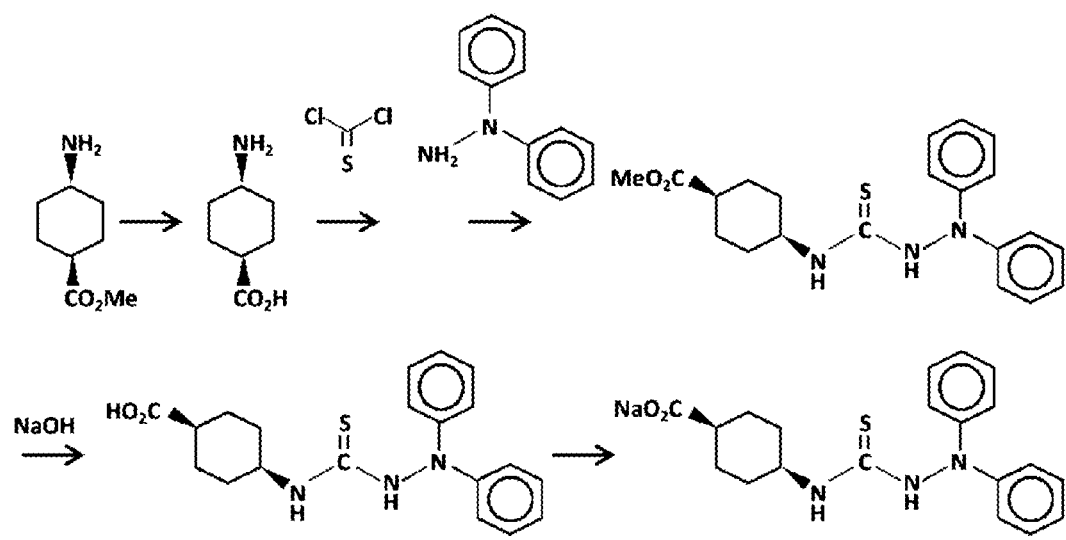

THERAPEUTIC AGENT FOR DIABETES

TECHNICAL FIELD

The present invention relates to a novel therapeutic agent for diabetes mellitus which can suppress the occurrence of side effects such as persistent hypoglycemia. More specifically, the present invention relates to a therapeutic agent for diabetes mellitus characterized in that the active ingredient is a derivative of 1,1-diphenylsemicarbazide or 1,1-diphenylthiosemicarbazide, such as 1,1-diphenyl-4-cyclohexyl-semicarbazide or 1,1-diphenyl-4-cyclohexyl-thiosemicarbazide.

BACKGROUND ART

Type 2 diabetes mellitus is a disease characterized by insulin secretion failure from pancreatic β cells and a decrease in insulin sensitivity of tissues including liver, adipose tissue and muscle. Various diabetes remedies have been developed that promote the secretion of insulin from pancreatic β cells and have a drug effect of improving insulin sensitivity in tissues. As an insulin secretion promoter, sulfonylurea (SU agent), gilded drug, incretions related drug, and the like are clinically applied as a therapeutic agent for type 2 diabetes accompanied by insulin secretion failure (Non-Patent Document 1). Of these, sulfonylureas are most widely used.

An ATP-sensitive potassium channel ($K_{ATP}$ channel) is expressed in pancreatic β-cells. The $K_{ATP}$ channel is composed of Kir6.2 which is a hole forming subunit, and SUR1 which is a control subunit (Non-Patent Documents 2 to 4). SUR1 is also a receptor for sulfonyl urea and glinide drugs.

Sulfonylureas and glinide drugs close the $K_{ATP}$ channel by binding to SUR1. As a result, the pancreatic β-cell membrane is depolarized, the voltage-dependent calcium channels (VDCCs) are released, the calcium ions flow, the calcium ion concentration in the pancreatic β cells rises, and insulin secretion is induced (Non-Patent Documents 5 to 8).

In addition to the function of closing the $K_{ATP}$ channel, sulfonylurea also has the function of directly activating Epac2A/Rap1 which is a signal molecule stimulating insulin secretion in pancreatic β cells (Non-Patent Documents 9 and 10, Patent Document 1). Activation of Epac2A by sulfonylurea is caused by cooperation of sulfonylurea and cAMP (Non-Patent Document 11).

Sulfonylureas and glinide drugs are widely used as therapeutic agents for type 2 diabetes. However, while these agents have a therapeutic effect of promoting the secretion of insulin, they may cause persistent hypoglycemia as a side effect. It is believed that the cause is that since these agents are stable in vivo, their action is sustained for a long time (Non-Patent Document 12). The side effect tends to occur particularly in elderly people and patients with renal failure, among diabetic patients. Therefore, there is a clinical need for new drugs of type 2 diabetes drugs, which have a low incidence of side effects such as hypoglycemia.

PRIOR ART DOCUMENTS

Patent Documents

[Patent Document 1] WO 2010/119693

Non-Patent Documents

[Non-patent Document 1] Stein S A. et al., Expert Opin Drug Saf. 12. 153-75 (2013)
[Non-patent Document 2] Inagaki N. et al., Science. 270. 1166-70 (1995)
[Non-patent Document 3] Sakura H. et al., FEBS letters. 367. 193-7 (1995)
[Non-patent Document 4] Seino S. Annu Rev Physiol. 61. 337-62 (1999)
[Non-patent Document 5] Ashcroft F M. et al., Prog Biophys Mol Biol. 54. 87-143 (1999)
[Non-patent Document 6] Aguilar-Bryan L. et al., Endocr Rev. 20. 101-35 (1999)
[Non-patent Document 7] Henquin J C. et al., Diabetes. 49. 1751-60 (2000)
[Non-patent Document 8] Seino S. et al., Prog Biophys Mol Biol. 81. 133-76 (2003)
[Non-patent Document 9] Zhang C L. et al., Science. 325. 607-10 (2009)
[Non-patent Document 10] Takahashi T. et al., Sci Signal. 6. Ra94. (2013)
[Non-patent Document 11] Takahashi H. et al., Diabetes. 64. 1262-72 (2015)
[Non-patent Document 12] Nyenwe E A. et al., Metabolism. 60. 1-23 (2011)

SUMMARY OF INVENTION

Technical Problem

An object of the present invention is to provide a novel oral hypoglycemic agent which can be used as a therapeutic agent for type 2 diabetes, while suppressing the occurrence of side effects such as persistent hypoglycemia and the like observed in the use of drugs such as sulfonylureas and glinide drugs.

Technical Solution

In research directed towards the above object, the present inventors have found a novel compound having a relatively short half-life in the blood and having an activity of promoting the secretion of insulin from pancreatic β cells and completed the present invention. That is, the present invention includes the following:

1. A compound represented by the following general formula (I):

(Chem. 1)

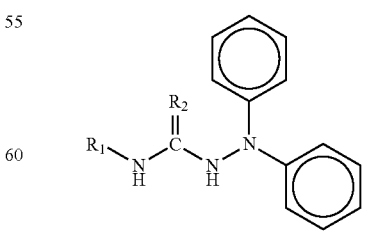

(I)

wherein $R_1$ represents a cyclohexyl group or a derivative thereof or an alkyl group of $CH_3-(CH_2)_n-$ (n=1 to 8), and $R_2$ represents an oxygen atom or a sulfur atom.

2. A compound according (1) above, represented by the following general formula [II]:

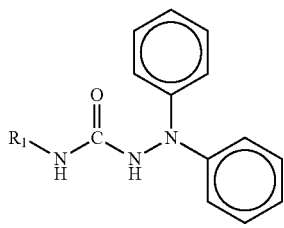

(Chem. 2)

(II)

wherein $R_1$ represents a cyclohexyl group or a derivative thereof or an alkyl group of $CH_3-(CH_2)_n-$ (n=1 to 8).

3. A compound according (1) above, represented by the following general formula [III]:

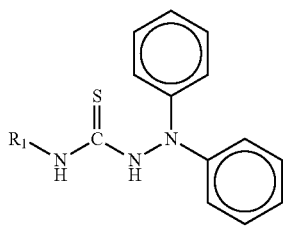

(Chem. 3)

(III)

wherein $R_1$ represents a cyclohexyl group or a derivative thereof or an alkyl group of $CH_3-(CH_2)_n-$ (n=1 to 8).

4. The compound according to any one of (1) to (3) above, wherein the derivative of the cyclohexyl group is selected from the group consisting of:
(1) a derivative wherein one hydrogen on the cyclohexyl ring is substituted with the group selected from the group consisting of a carboxyl group, a carboxymethyl group, a carboxypentyl group, a hydroxy group, and an acetyl group, or a salt thereof;
(2) a derivative wherein two hydrogens on the cyclohexyl ring is independently substituted with the group selected from the group consisting of a carboxyl group, a carboxymethyl group, a carboxyethyl group, a carboxypentyl group, a hydroxy group, and an acetyl group, or a salt thereof;
(3) a derivative wherein three hydrogens on the cyclohexyl ring is independently substituted with the group selected from the group consisting of a carboxyl group, a carboxymethyl group, a carboxypentyl group, a hydroxy group, and an acetyl group, or a salt thereof;
(4) a derivative wherein one to three of the six carbon atoms constituting the cyclohexyl ring are substituted with nitrogen atoms;
(5) a derivative wherein one of the six carbon atoms constituting the cyclohexyl ring is substituted with a nitrogen atom;
(6) a derivative introduced the substitution of (4) above combined with any one of the substitutions of (1) to (3) above;
(7) a derivative introduced the substitution of (5) above combined with any one of the substitutions of (1) to (3) above.

5. The compound according to (4) above, wherein the salt is a sodium salt or a potassium salt.

6. The compound according to (1) above, represented by the following general formula (IV):

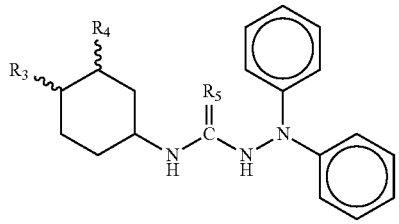

(Chem. 4)

(IV)

wherein $R_3$ and $R_4$ independently represent a group or an atom selected from the group consisting of a carboxyl group, a carboxymethyl group, a carboxypentyl group, a hydroxy group, an acetyl group, and a hydrogen atom, or a salt thereof, $R_5$ represents an oxygen atom or a sulfur atom, and $R_3$ is coordinated to cis (cis-) or trans (trans-) with 1,1-diphenyl semicarbazide group.

7. The compound according to (6) above, represented by the following general formula (V):

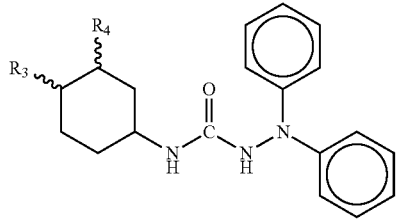

(Chem. 5)

(V)

wherein $R_3$ and $R_4$ independently represent a group or an atom selected from the group consisting of a carboxyl group, a carboxymethyl group, a carboxypentyl group, a hydroxy group, an acetyl group and a hydrogen atom, or a salt thereof, and $R_3$ is coordinated to cis (cis-) or trans (trans-) with 1,1-diphenyl semicarbazide group.

8. The compound according to (6) above, represented by the following general formula (VI):

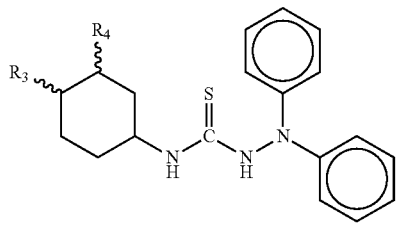

(Chem. 6)

(VI)

wherein $R_3$ and $R_4$ independently represent a group or an atom selected from the group consisting of a carboxyl group, a carboxymethyl group, a carboxypentyl group, a hydroxy group, an acetyl group and a hydrogen atom, or a salt thereof, and R₃ is coordinated to cis (cis-) or trans (trans-) with 1,1-diphenyl semicarbazide group.

9. The compound according to (6) above, represented by the following general formula (VII):

(Chem. 7)

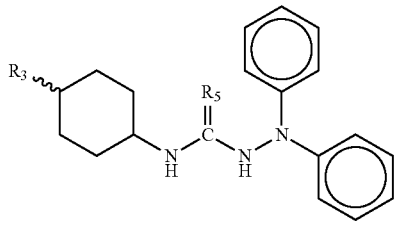

(VII)

wherein R₃ represents a group selected from the group consisting of a carboxyl group, a carboxymethyl group, a carboxypentyl group, a hydroxy group, and an acetyl group, or a salt thereof, R₅ represents an oxygen atom or a sulfur atom, and R₃ is coordinated to cis (cis-) or trans (trans-) with 1,1-diphenyl semicarbazide group.

10. The compound according to (9) above, represented by the following general formula (VIII):

(Chem. 8)

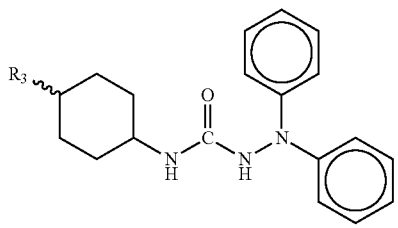

(VIII)

wherein R₃ represents a group selected from the group consisting of a carboxyl group, a carboxymethyl group, a carboxypentyl group, a hydroxy group, and an acetyl group, or a salt thereof, and R₃ is coordinated to cis (cis-) or trans (trans-) with 1,1-diphenyl semicarbazide group.

11. The compound according to (9) above, represented by the following general formula (IX):

(Chem. 9)

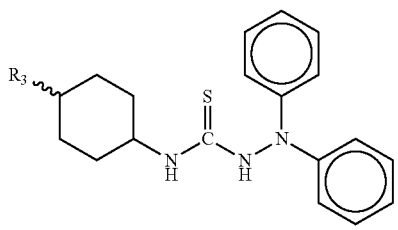

(IX)

wherein R₃ represents a group selected from the group consisting of a carboxyl group, a carboxymethyl group, a carboxypentyl group, a hydroxy group, and an acetyl group, or a salt thereof, and R₃ is coordinated to cis (cis-) or trans (trans-) with 1,1-diphenyl semicarbazide group.

12. The compound according to any one of (6) to (11) above, wherein R₃ represents a carboxyl group or a salt thereof in the general formulas [IV] to [IX].

13. The compound according to any one of (6) to (12) above, wherein the salt is a sodium salt or a potassium salt in the general formulas [IV] to [IX].

14. The compound according to (13) above, wherein the salt is a sodium salt.

15. The compound according to (10) above, represented by the following general formula (X):

(Chem. 10)

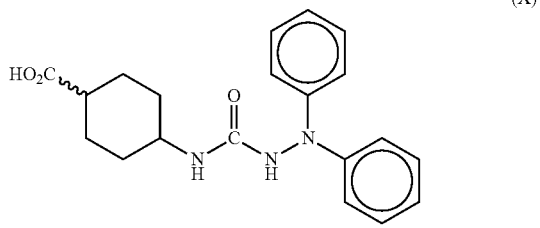

(X)

wherein the carboxyl group and the 1,1-diphenylsemicarbazide group are coordinated to cis (cis-) or trans (trans-).

16. The compound according to (11) above, represented by the following general formula (XI):

(Chem. 11)

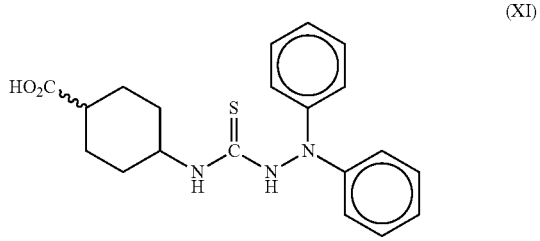

(XI)

wherein the carboxyl group and the 1,1-diphenylsemicarbazide group are coordinated to cis (cis-) or trans (trans-).

17. The compound according to (16) above, represented by the following general formula (XII) or the salt thereof.

(Chem. 12)

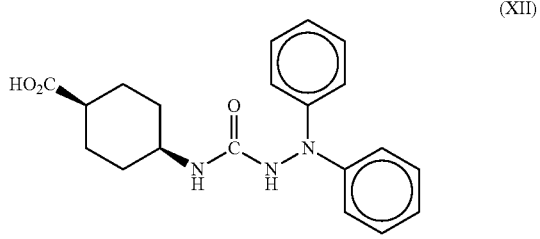

(XII)

18. The compound according to (16) above, represented by the following general formula (XIII) or the salt thereof.

(Chem. 13)

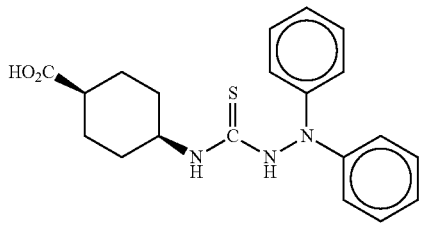

(XIII)

19. A compound according to any one of (15) to (18) above, wherein the salt is a sodium salt or potassium salt.
20. The compound according to (1) above, represented by the following general formula (XXI):

(Chem. 21)

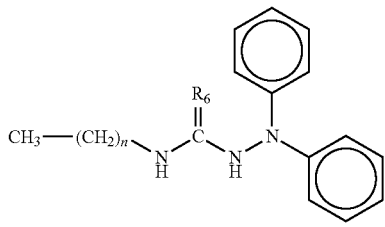

(XXI)

wherein, n is an integer of 1 to 6 indicating the alkyl chain length, and $R_6$ represents an oxygen atom or a sulfur atom.
21. The compound according to (20) above, represented by the following general formula (XXII):

(Chem. 22)

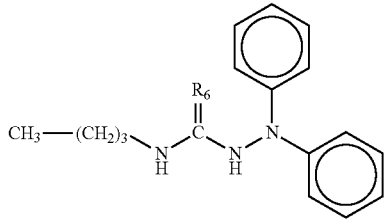

(XXII)

wherein, $R_6$ represents an oxygen atom or a sulfur atom.
22. A pharmaceutical composition comprising the compound according to any one of (1) to (21) above as an active ingredient.
23. The pharmaceutical composition according to (21) above, wherein the composition is used for treating diabetes.
24. The pharmaceutical composition according to (22) above, wherein the diabetes is type 2 diabetes.
25. The pharmaceutical composition according to any one of (22) to (24) above, wherein the composition is used for the treatment of a patient experiencing persistent hypoglycemia by administration of a sulfonylurea.
26. The pharmaceutical composition according to any one of (22) to (25) above, wherein the composition is orally administered.
27. The pharmaceutical composition according to any one of (22) to (26) above, wherein a dosage thereof is 1 to 100 mg/kg body weight.

Effect of Invention

According to the present invention, it is possible to provide a therapeutic agent for type 2 diabetes showing reduced side effects such as persistent hypoglycemia.

BRIEF DESCRIPTION OF DRAWINGS

FIG. 1 shows the results of an insulin secretion stimulation test using MIN6-K8 cells. The vertical axis shows the relative amount of secreted insulin to the control. The horizontal axis shows the concentration of the test compound. C8 for white bars and DSC108 for black bars indicate the values when used as test compounds. The vertical line of each measured value indicates standard deviation. An asterisk indicates P<0.05, and a double asterisk indicates a significant difference of P<0.01 (unpaired student t test).

FIG. 2 shows the results of an insulin secretion stimulation test using a mouse. The vertical axis shows the concentration (ng/mL) of insulin contained in the perfusion liquid. The horizontal axis shows the elapsed time (minutes) after the start of perfusion. The vertical line of each measured value indicates standard deviation.

FIG. 3 shows the measurement results of intracellular calcium ion concentration. The vertical axis shows the value of (fluorescence intensity at 340 nm/fluorescence intensity at 380 nm). The horizontal axis shows the elapsed time (minutes) after addition of the DSC108. Black circles indicate measured values when DSC108 of 30 μM, black squares indicate DSCs of 10 μM, black triangles measured values of DSCs of 3 μM, respectively. The vertical line of each measured value indicates standard deviation.

FIG. 4 shows the results of [$^3$H] glibenclamide competition test. The vertical axis shows the binding amount (%) of [$^3$H] glibenclamide to MIN6-K8 cells when the control is 100%. The horizontal axis shows the log value (M) of the concentration of added DSC108-Na. The vertical line of each measured value indicates standard deviation.

FIG. 5 shows measurement results of blood concentration of DSC108-Na. The vertical axis shows the plasma compound concentration (μM) of the test compound. The horizontal axis shows the elapsed time (minutes) after administration of the test compound. The black circle indicates the concentration (μM) of DSC108-Na, and the open circle indicates the concentration (μM) of gliclazide. The vertical line of each measured value indicates standard deviation.

FIG. 6 shows measurement results of hypoglycemic action using a wild-type mouse. The vertical axis shows blood glucose concentration (mg/dL). The horizontal axis shows elapsed time (minutes) after administration of DSC108-Na. The white circles indicate the measurement values in the vehicle administration group (control group), the black squares indicate the 10 mg/kg body weight administration group, the black triangles 30 mg/kg body weight administration group, and the black circles 100 mg/kg body weight administration group. The vertical line of each measured value indicates standard deviation. An asterisk indicates P<0.05, and a double asterisk indicates a significant difference of P<0.01 (Dunnett's test).

FIG. 7 shows measurement results of hypoglycemic action using type 2 diabetes model rats. The vertical axis shows insulin concentration (ng/mL) in plasma. The horizontal axis shows elapsed time (minutes) after administration of DSC108-Na. White circles represent the vehicle administration group, and black circles represent the measurement values of the DSC108-Na administration group, respectively. The vertical line of each measured value indicates standard deviation. The asterisk indicates a significant difference of P<0.05 in the t test (paired student's t test).

FIG. 8 shows measurement results of hypoglycemic action using type 2 diabetes model rats. The vertical axis shows blood glucose concentration (mg/dL). The horizontal axis shows elapsed time (minutes) after administration of DSC108-Na. White circles represent the vehicle administration group, and black circles represent the measurement values of the DSC108-Na administration group, respectively. The vertical line of each measured value indicates standard deviation. The asterisk indicates a significant difference of P<0.05 (Pair-Student t test).

FIG. 9 shows the results of an insulin secretion stimulation test using MIN6-K8 cells of derivatives of various 1,1-diphenylsemicarbazide. The vertical axis shows the relative amount of secreted insulin to the control. The numbers on the horizontal axis correspond to the numbers of the compounds shown in Table 1. The vertical line of each measured value indicates standard deviation.

FIG. 10 is a schematic view showing an example of a method for producing DSC108 and its sodium salt.

DESCRIPTION OF EMBODIMENTS

"Semicarbazide" is a substance represented by chemical formula (14), and "thiosemicarbazide" is a substance represented by chemical formula (15). Sulfonylurea is used as a therapeutic agent for type 2 diabetes as a substance promoting insulin secretion. The sulfonylurea has a sulfonylurea structure (S-phenylsulfonylurea structure) represented by the chemical formula (16). Therefore, sulfonylurea can be regarded as a derivative of semicarbazide.

[Chem. 14]

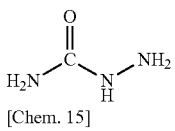

(XIV)

[Chem. 15]

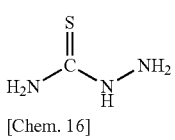

(XV)

[Chem. 16]

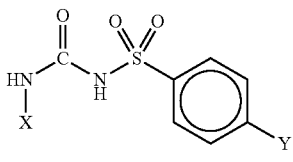

(XVI)

(X and Y denote functional groups)

The compound according to the present invention was obtained by screening candidate substances having insulin secretion promoting activity, while an attention has been paid attention to that sulfonylurea is a derivative of semicarbazide. That is, the compound of the present invention is a derivative of semicarbazide or thiosemicarbazide.

More specifically, the semicarbazide derivative of the present invention is a derivative of 1,1-diphenylsemicarbazide represented by the chemical formula (17). In the present invention, a portion of the chemical formula (17) excluding $R_1$ is referred to as a 1,1-diphenylsemicarbazide group.

[Chem. 17]

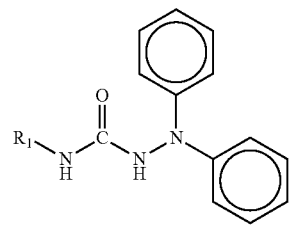

(XVII)

In the chemical formula (17), there is no particular limitation as to $R_1$, but a cyclohexyl group or a derivative thereof is preferable. Examples of the derivatives of cyclohexyl group include:

(1) a derivative in which one hydrogen atom on the cyclohexyl ring is substituted with a group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl Group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 3,4-dicarboxypentyl group, a 2,5-dicarboxypentyl group, a 4,5-dicarboxypentyl group, a 1,2-dicarboxyhexyl group, a 1,3-dicarboxyhexyl, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group (in particular those in which a hydrogen in the meta position (m-) or the para position (p-) is replaced by any of groups), or a salt thereof;

(2) a derivative in which two hydrogen atoms on the cyclohexyl ring are substituted, respectively, with a group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl Group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl group, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group (in particular, those in which a hydrogen in the meta position (m-) or para position (p-) is replaced by any of groups), or a salt thereof;

(3) a derivative in which three hydrogen atoms on the cyclohexyl ring are substituted, respectively, with a group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl Group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group (in particular, those in which a hydrogen in the meta position (m-) or para position (p-) are replaced by any of groups), or a salt thereof;

(4) a derivative in which 1 to 3 carbons of 6 carbons constituting the cyclohexyl ring are replaced by nitrogens;

(5) a derivatives in which one carbon of 6 carbons constituting the cyclohexyl ring is replaced by a nitrogen;

(6) a derivative wherein the above (4) and any one of the above (1) to (3) are combined;

(7) a derivative wherein the above (5) and any one of the above (1) to (3) are combined, or a salt thereof.

In this, as the salt, a sodium salt or a potassium salt is preferable, and a sodium salt is more preferable, but there is no particular limitation as to the salt. Further, the group replaced by hydrogen on the cyclohexyl ring may be bonded to the axial position or to the equatorial position when the 1,1-diphenylthiosemicarbazide group is bonded to the equatorial position. That is, these groups may coordinate to cis (cis-) or to trans (trans-) with the 1,1-diphenylthiosemicarbazide group on the cyclohexyl ring.

A more specific form of the semicarbazide derivative, in the chemical formula (17), include the derivative in which $R_1$ is selected from the group consisting of a cyclohexyl group, a 3-carboxycyclohexyl group, a 4-carboxycyclohexyl group, a 2,4-dicarboxycyclohexyl group, a 3,4-dicarboxycyclohexyl group, a 2,4,6-tricarboxycyclohexyl group, a 3-carboxymethylcyclohexyl group, a 4-carboxymethylcyclohexyl group, a 2,4-dicarboxymethylcyclohexyl group, a 3,4-dicarboxymethylcyclohexyl group, a 2,4,6-tricarboxymethylcyclohexyl group, a 3-carboxyethylcyclohexyl group, a 4-carboxyethylcyclohexyl group, a 2,4-dicarboxyethylcyclohexyl group, a 3,4-dicarboxyethylcyclohexyl group, a 2,4,6-tricarboxyethylcyclohexyl group, a 3-carboxypropylcyclohexyl group, a 4-carboxypropylcyclohexyl group, a 2,4-dicarboxypropylcyclohexyl group, a 3,4-dicarboxypropylcyclohexyl group, a 2,4,6-tricarboxypropylcyclohexyl group, a 3-carboxypentylcyclohexyl group, a 4-carboxypentylcyclohexyl group, a 2,4-dicarboxypentylcyclohexyl group, a 3,4-dicarboxypentylcyclohexyl group, a 2,4,6-tricarboxypentylcyclohexyl group, a 3-carboxy-4-carboxymethylcyclohexyl group, a 3-carboxy-4-carboxyethylcyclohexyl group, a 3-carboxy-4-carboxybutylcyclohexyl group, a 3-carboxy-4-carboxypentylcyclohexyl group, a 3-carboxymethyl-4-carboxycyclohexyl group, a 3-carboxyethyl-4-carboxycyclohexyl group, a 3-carboxybutyl-4-carboxycyclohexyl group, a 3-carboxypentyl-4-carboxycyclohexyl group, a 3-hydroxycyclohexyl group, a 4-hydroxycyclohexyl group, a 2,4-dihydroxycyclohexyl group, a 3,4-dihydroxycyclohexyl group, a 2,4,6-trihydroxycyclohexyl group, a 2-hydroxy-4-carboxycyclohexyl group, a 3-hydroxy-4-carboxycyclohexyl group, a 3,5-dihydroxy-4-carboxycyclohexyl group, a 2-hydroxy-4-carboxymethylcyclohexyl group, a 3-hydroxy-4-carboxymethylcyclohexyl group, a 3,5-dihydroxy-4-carboxymethylcyclohexyl group, a 2-hydroxy-4-carboxyethylcyclohexyl group, a 3-hydroxy-4-carboxyethylcyclohexyl group, a 3,5-dihydroxy-4-carboxyethylcyclohexyl group, a 2-hydroxy-4-carboxypentylcyclohexyl group, a 3,5-dihydroxy-4-carboxypentylcyclohexyl group, a 3-hydroxymethylcyclohexyl group, a 4-hydroxymethylcyclohexyl group, a 2,4-dihydroxymethylcyclohexyl group, a 2,4-dihydroxymethylcyclohexyl group, a 3,4-dihydroxymethylcyclohexyl group, a 2,4,6-trihydroxymethylcyclohexyl group, a 2-hydroxymethyl-4-carboxycyclohexyl group, a 3-hydroxymethyl-4-carboxycyclohexyl group, a 3,5-dihydroxymethyl-4-carboxycyclohexyl group, a 2-hydroxymethyl-4-carboxymethylcyclohexyl group, a 3-hydroxymethyl-4-carboxymethylcyclohexyl group, a 3,5-dihydroxymethyl-4-carboxymethylcyclohexyl group, a 2-hydroxymethyl-4-carboxyethylcyclohexyl group, a 3-hydroxymethyl-4-carboxyethylcyclohexyl group, a 3,5-dihydroxymethyl-4-carboxyethylcyclohexyl group, a 2-hydroxymethyl-4-carboxypentylcyclohexyl group, a 3-hydroxymethyl-4-carboxypentylcyclohexyl group, a 3,5-dihydroxymethyl-4-carboxypentylcyclohexyl group, a 2-hydroxyethyl-4-carboxycyclohexyl group, a 3-hydroxyethyl-4-carboxycyclohexyl group, a 3,5-dihydroxyethyl-4-carboxycyclohexyl group, a 2-hydroxyethyl-4-carboxymethylcyclohexyl group, a 3-hydroxyethyl-4-carboxymethylcyclohexyl group, a 3,5-dihydroxyethyl-4-carboxymethylcyclohexyl group, a 2-hydroxyethyl-4-carboxyethylcyclohexyl group, a 3,5-dihydroxyethyl-4-carboxyethylcyclohexyl group, a 2-hydroxyethyl-4-carboxypentylcyclohexyl group, a 3-hydroxyethyl-4-carboxypentylcyclohexyl group, a 3,5-dihydroxyethyl-4-carboxypentylcyclohexyl group, a 3-(1-hydroxypropyl)cyclohexyl group, a 4-(1-hydroxypropyl)cyclohexyl group, a 3-(1-hydroxypropyl)-4-carboxycyclohexyl group, a 4-(1-hydroxypropyl)-4-carboxycyclohexyl group, a 3-(2-hydroxypropyl)cyclohexyl group, a 4-(2-hydroxypropyl)cyclohexyl group, a 3-(2-hydroxypropyl)-4-carboxycyclohexyl group, a 4-(2-hydroxypyl)-4-carboxycyclohexyl group, a 3-(3-hydroxypropyl)cyclohexyl group, a 4-(3-hydroxypropyl)cyclohexyl group, a 3-(3-hydroxypropyl)-4-carboxycyclohexyl group, a 4-(3-hydroxypropyl)-4-carboxycyclohexyl group, a 3-(1-hydroxybutyl)-4-carboxycyclohexyl group, a 4-(1-hydroxybutyl)-4-carboxycyclohexyl group, a 3-(2-hydroxybutyl)cyclohexyl group, a 4-(2-hydroxybutyl)cyclohexyl group, a 3-(2-hydroxybutyl)cyclohexyl group, a 4-(2-hydroxybutyl)-4-carboxycyclohexyl group, a 3-(3-hydroxybutyl)cyclohexyl group, a 4-(3-hydroxybutyl)cyclohexyl group, a 3-(3-hydroxybutyl)-4-carboxycyclohexyl group, a 4-(4-hydroxybutyl)cyclohexyl group, a 3-(4-hydroxybutyl)-4-carboxycyclohexyl group, a 4-(4-hydroxybutyl)-4-carboxycyclohexyl group, a 3-(1-hydroxypentyl)cyclohexyl group, a 4-(1-hydroxypentyl)cyclohexyl group, a 3-((l-hydroxypentyl)-4-carboxycyclohexyl group, a 4-(1-hydroxypentyl)-4-carboxycyclohexyl group, a 3-(2-hydroxypentyl)cyclohexyl group, a 4-(2-hydroxypentyl)cyclohexyl group, a 3-(2-hydroxypentyl)-4-carboxycyclohexyl group, a 4-(2-hydroxypentyl)-4-carboxycyclohexyl group, a 3-(3-hydroxypentyl)cyclohexyl group, a 4-(3-hydroxypentyl)cyclohexyl group, a 3-(3-hydroxypentyl)-4-carboxycyclohexyl group, a 4-(3-hydroxypentyl)-4-carboxycyclohexyl group, a 3-(4-hydroxypentyl)cyclohexyl group, a 4-(4-hydroxypentyl)cyclohexyl group, a 4-(4-hydroxypentyl)-4-carboxycyclohexyl group, a 3-(5-hydroxypentyl)cyclohexyl group, a 4-(5-hydroxypentyl)-4-carboxycyclohexyl group, a 3-(5-hydroxypentyl)-4-carboxycyclohexyl group, a 4-(5-hydroxypentyl)-4-carboxycyclohexyl group, a 3-sulfocyclohexyl group, a 4-sulfocyclohexyl group, a 2,4-sulfocyclohexyl group, a 2,4-sulfocyclohexyl group, a 3,4-disulfocyclohexyl group, a 2-sulfo-4-carboxycyclohexyl group, a 3-sulfo-4-carboxycyclohexyl group, a 3,5-disulfo-4-carboxycyclohexyl group, a 2-sulfo-4-carboxymethylcyclohexyl group, a 3-sulfo-4-carboxymethylcyclohexyl group, a 3,5-disulfo-4-carboxymethylcyclohexyl group, a 2-sulfo-4-carboxyethylcyclohexyl group, a 3-sulfo-4-carboxyethylcyclohexyl group, a 3,5-disulfo-4-carboxyethylcyclohexyl group, a 2-sulfo-4-carboxypentylcyclohexyl group, a 3-sulfo-4-carboxypentylcyclohexyl group, a and 3,5-disulfo-4-carboxypentylcyclohexyl group, or a salt thereof. As the salt, a sodium salt or a potassium salt is preferable, and a sodium salt is more preferable, but there is no particular limitation as to the salt. Further, the group on the cyclohexyl ring may be bonded to the axial position or to the equatorial position when the 1,1-diphenylthiosemicarbazide group is bonded to the equatorial position. That is, these groups may coordinate to cis (cis-) or to trans (trans-) with the 1,1-diphenylthiosemicarbazide group on the cyclohexyl ring.

A preferred form of the semicarbazide derivative of the present invention is 1,1-diphenyl-4-cyclohexyl-semicarbazide represented by the chemical formula (18), wherein $R_1$ in the chemical formula (17) is a cyclohexyl group.

[Chem. 18]

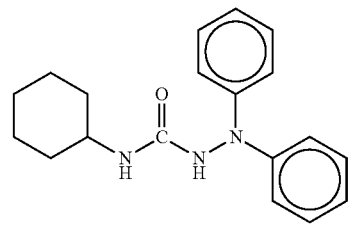

(XVIII)

A further preferred embodiment of the semicarbazide derivative of the present invention is represented by the chemical formula (5). In this, $R_3$ and $R_4$ each independently represents a group or an atom selected from the group consisting of a carboxyl group, a carboxymethyl group, a carboxypentyl group, a hydroxy group, an acetyl group, and a hydrogen atom or a salt thereof. $R_3$ may be bonded to the axial position or to the equatorial position in the cyclohexyl ring. That is, $R_3$ may coordinate to cis (cis-) or to trans (trans-) with the 1,1-diphenylthiosemicarbazide group on the cyclohexyl ring.

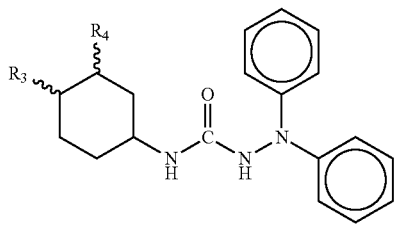

(V)

A further preferred form of the semicarbazide derivative of the present invention is represented by the chemical formula (8). In this, $R_3$ represents a group selected from the group consisting of carboxyl group, carboxymethyl group, carboxypentyl group, hydroxy group, and acetyl group, or a salt thereof. $R_3$ may be bonded to the axial position or to the equatorial position in the cyclohexyl ring. That is, $R_3$ may coordinate to cis (cis-) or to trans (trans-) with the 1,1-diphenylthiosemicarbazide group on the cyclohexyl ring.

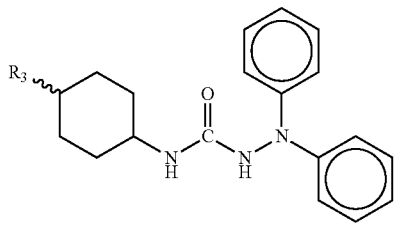

(VIII)

As a further preferred embodiment of the semicarbazide derivative of the present invention, there is 1,1-diphenyl-4-(4-carboxycyclohexyl)-semicarbazide represented by the chemical formula (10), in that formula, $R_1$ in the chemical formula (17) is 4-carboxycyclohexyl group. In this, the carboxy group may be bonded to the axial position in the cyclohexyl ring or to the equatorial position. That is, the carboxy group may coordinate to cis (cis-) or to trans (trans-) with the 1,1-diphenylthiosemicarbazide group on the cyclohexyl ring, but is preferably the group coordinates to cis (cis-) as represented by the chemical formula (12)

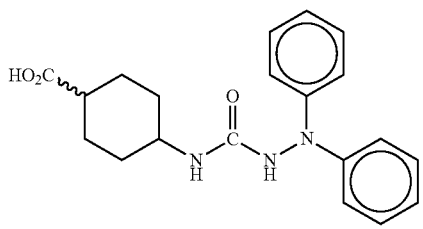

(X)

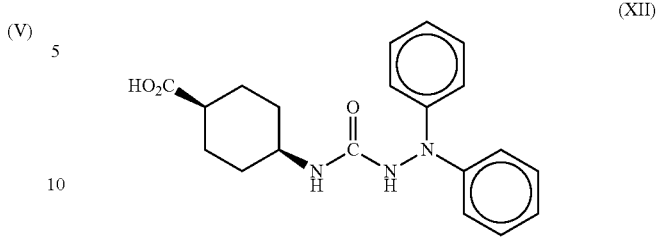

(XII)

In the semicarbazide derivatives represented by the chemical formulas (10), (12), (17) and (18), the hydrogen atom of the phenyl group in the 1,1-diphenylsemicarbazide group can be substituted with a functional group. The chemical formula (23) is such a derivative as one of hydrogen atoms of each of two phenyl groups in the 1,1-diphenylsemicarbazide group is substituted. X and Y in the formula, respectively, represent a functional group (substituent) independent from each other. In chemical formula (23), however, only one of X and Y may be substituted with a functional group, and both of X and Y may be substituted with a functional group.

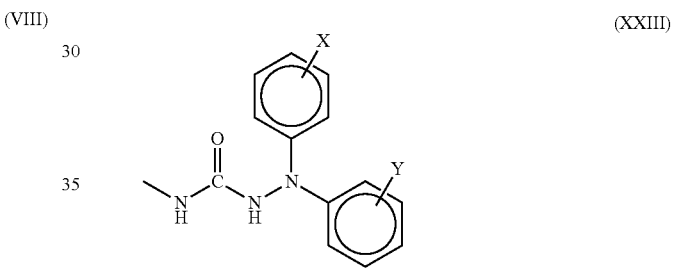

(XXIII)

Preferable examples of the functional group represented by X and Y in the chemical formula (23) include the functional group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl group, a 2,2-dicarboxyethyl group, a 2,3-dicarboxypropyl group, a 1,2-dicarboxypropyl group, a 3,2-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl group, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-dihydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group, or a salt thereof. There is no particular limitation as to the salt, but a sodium salt or a potassium salt is preferable, and a sodium salt is particularly preferable.

The thiosemicarbazide derivative of the present invention is a derivative of 1,1-diphenylthiosemicarbazide represented by the chemical formula (19). In the present invention, a portion of the chemical formula (19) excluding $R_1$ is referred to as a 1,1-diphenylthiosemicarbazide group.

[Chem. 19]

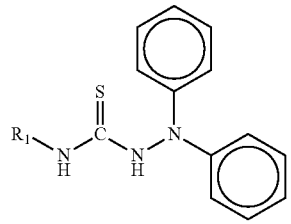

(XIX)

In the chemical formula (19), there is no particular limitation as to $R_1$, but a cyclohexyl group or a derivative thereof is preferable. Examples of the derivatives of cyclohexyl group include:

(1) a derivative in which one hydrogen atom on the cyclohexyl ring is substituted with a group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl Group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group (in particular those in which a hydrogen in the meta position (m-) or the para position (p-) is replaced by any of groups), or a salt thereof;

(2) a derivative in which two hydrogen atoms on the cyclohexyl ring are substituted, respectively, with a group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl Group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl group, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group (in particular, those in which a hydrogen in the meta position (m-) or para position (p-) are replaced by any of groups), or a salt thereof;

(3) a derivative in which three hydrogen atoms on the cyclohexyl ring are substituted, respectively, with a group selected from the group consisting of a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl Group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group (in particular, those in which a hydrogen in the meta position (m-) or para position (p-) are replaced by any of groups), or a salt thereof;

(4) a derivative in which 1 to 3 carbons of 6 carbons constituting the cyclohexyl ring are replaced by nitrogens;

(5) a derivatives in which one carbon of 6 carbons constituting the cyclohexyl ring is replaced by a nitrogen;

(6) a derivative wherein the above (4) and any one of the above (1) to (3) are combined;

(7) a derivative wherein the above (5) and any one of the above (1) to (3) are combined, or a salt thereof.

In this, as the salt, a sodium salt or a potassium salt is preferable, and a sodium salt is more preferable, but the salt is not limited thereto. Further, the group on the cyclohexyl ring may be bonded to the axial position or to the equatorial position when the 1,1-diphenylthiosemicarbazide group is bonded to the equatorial position. That is, these groups may coordinate to cis (cis-) or to trans (trans-) with the 1,1-diphenylthiosemicarbazide group on the cyclohexyl ring.

More specific form of the thiosemicarbazide derivative include, in the chemical formula (19), that derivative in which $R_1$ is a group selected from the group consisting of a cyclohexyl group, a 3-carboxycyclohexyl group, a 4-carboxycyclohexyl group, a 2,4-dicarboxycyclohexyl group, a 3,4-cyclohexyl group, a 2,4,6-tricarboxy cyclohexyl group, a 3-carboxymethyl cyclohexyl group, a 4-carboxymethyl cyclohexyl group, a 2,4-dicarboxymethyl cyclohexyl group, a 3,4-dicarboxymethyl cyclohexyl group, a 2,4,6-tricarboxymethylcyclohexyl group, a 3-carboxyethylcyclohexyl group, a 4-carboxyethylcyclohexyl group, a 2,4-dicarboxyethylcyclohexyl group, a 3,4-dicarboxyethylcyclohexyl group, a 2,4,6-tricarboxyethyl cyclohexyl group, a 3-carboxypropyl cyclohexyl group, a 4-carboxypropyl cyclohexyl group, a 2,4-dicarboxypropyl cyclohexyl group, a 3,4-dicarboxypropyl cyclohexyl group, a 2,4,6-tricarboxypropyl cyclohexyl group, a 3-carboxypentyl cyclohexyl group, a 4-carboxypentyl cyclohexyl group, a 2,4-dicarboxypentyl cyclohexyl group, a 3,4-dicarboxypentyl cyclohexyl group, a 2,4,6-tricarboxypentyl cyclohexyl group, a 3-carboxy-4-carboxymethyl cyclohexyl group, a 3-carboxy-4-carboxyethyl cyclohexyl group, a 3-carboxy-4-carboxybutyl cyclohexyl group, a 3-carboxy-4-carboxypentylcyclohexyl group, a 3-carboxymethyl-4-carboxycyclohexyl group, a 3-carboxyethyl-4-carboxycyclohexyl group, a 3-carboxybutyl-4-carboxycyclohexyl group, a 3-carboxypentyl-4-carboxycyclohexyl group, a 3-hydroxycyclohexyl group, a 4-hydroxycyclohexyl group, a 2,4-dihydroxycyclohexyl group, a 3,4-dihydroxycyclohexyl group, a 2,4,6-trihydroxycyclohexyl group, a 2-hydroxy-4-carboxycyclohexyl group, a 3-hydroxy-4-carboxycyclohexyl group, a 3,5-dihydroxy-4-carboxycyclohexyl group, a 2-hydroxy-4-carboxymethylcyclohexyl group, a 3-hydroxy-4-carboxymethylcyclohexyl group, a 3,5-dihydroxy-4-carboxymethylcyclohexyl group, a 2-hydroxy-4-carboxyethylcyclohexyl group, a 3-hydroxy-4-carboxyethylcyclohexyl group, a 3,5-dihydroxy-4-carboxyethylcyclohexyl group, a 2-4-carboxypentylcyclohexyl group, a 3,5-dihydroxy-4-carboxypentylcyclohexyl group, a 3-hydroxymethylcyclohexyl group, a 4-hydroxymethylcyclohexyl group, a 2,4-dihydroxymethylcyclohexyl group, a 2,4-dihydroxymethylcyclohexyl group, a 3,4-dihydroxymethylcyclohexyl group, a 2,4,6-trihydroxymethylcyclohexyl group, a 2-hydroxymethyl-4-carboxycyclohexyl group, a 3-hydroxymethyl-4-carboxycyclohexyl group, a 3,5-dihydroxymethyl-4-carboxycyclohexyl group, a 2-hydroxymethyl-4-carboxymethylcyclohexyl group, a 3-hydroxymethyl-4-carboxymethylcyclohexyl group, a 3,5-dihydroxymethyl-4-carboxymethylcyclohexyl group, a 2-hydroxymethyl-4-carboxyethylcyclohexyl group, a 3-hydroxymethyl-4-carboxyethylcyclohexyl group, a 3,5-dihydroxymethyl-4-carboxyethylcyclohexyl group, a 2-hydroxymethyl-pentylcyclohexyl group, a 3-hydroxymethyl-4-carboxypentylcyclohexyl group, a 3,5-dihydroxymethyl-4-carboxypentylcyclohexyl group, a 2-hydroxyethyl-4-carboxycyclohexyl group, a 3-hydroxyethyl-4-carboxycyclohexyl group, a 3,5-dihydroxyethyl-4-carboxycyclohexyl group, a 2-hydroxyethyl-4-carboxymethylcyclohexyl group, a 3-hydroxyethyl-4-carboxymethylcyclohexyl group, a 3,5-dihydroxyethyl-4-carboxy Methylcyclohexyl, a 2-hydroxyethyl-4-carboxyethylcyclohexyl group, a 3-hydroxyethyl-4-carboxyethylcyclohexyl group, a 3,5-dihydroxyethyl-4-carboxyethylcyclohexyl group, a 2-hydroxyethyl-4-carboxypentylcyclohexyl group, a 3-hydroxyethyl-4-carboxypentylcyclohexyl group, a 3,5-dihydroxyethyl-4-carboxypentylcyclohexyl group, a 3-(1-hydroxypropyl)cyclohexyl group, a 4-(1-hydroxypropyl)cyclohexyl group, a 3-(1-hydroxypropyl)-4-carboxycyclohexyl group, a 3-(2-hydroxypropyl)cyclohexyl group, a 4-(2-hydroxypropyl)cyclohexyl group, a 3-(2-hydroxypropyl)-4-carboxycyclohexyl group, a 4-(2-hydroxypropyl)-4-carboxycyclohexyl group, a 3-(3-hydroxypropyl)cyclohexyl group, a 4-(3-hydroxypropyl)cyclohexyl group, a 3-(3-hydroxypropyl)-4-carboxycyclohexyl group, a 4-(3-hydroxypropyl)-4-carboxycyclohexyl group, a 3-(1-hydroxybutyl)cyclohexyl group, a 4-(1-hydroxybutyl)cyclohexyl group, a 3-(1-hydroxybutyl)-4-carboxycyclohexyl group, a 4-(1-hydroxybutyl)-4-carboxycyclohexyl group, a 3-(2-hydroxybutyl)cyclohexyl group, a 4-(2-hydroxybutyl)cyclohexyl group, a 3-(2-hydroxybutyl)-4-carboxycyclohexyl group, a 4-(2-hydroxybutyl)-4-carboxycyclohexyl group, a 3-(3-hydroxybutyl)cyclohexyl group, a 4-(3-hydroxybutyl)cyclohexyl group, a 3-(3-hydroxybutyl)-4-carboxycyclohexyl group, a 4-(3-hydroxybutyl)-4-carboxycyclohexyl group, a 3-(4-hydroxybutyl)cyclohexyl group, a 4-(4-hydroxybutyl)cyclohexyl group, a 3-(4-hydroxybutyl)-4-carboxycyclohexyl group, a 4-(4-hydroxybutyl)-4-carboxycyclohexyl group, a 3-(1-hydroxypentyl)cyclohexyl group, a 4-(1-hydroxypentyl)cyclohexyl group, a 3-(1-hydroxypentyl)-4-carboxycyclohexyl group, a 4-(1-hydroxypentyl)-4-carboxycyclohexyl group, a 3-(2-hydroxypentyl)cyclohexyl group, a 4-(2-hydroxypentyl)cyclohexyl group, a 3-(2-hydroxypentyl)-4-carboxycyclohexyl group, a 4-(2-hydroxypentyl)-4-carboxycyclohexyl group, a 3-(3-hydroxypentyl)cyclohexyl group, a 4-(3-hydroxypentyl)-cyclohexyl group, a 3-(3-hydroxypentyl)-4-carboxycyclohexyl group, a 4-(3-hydroxypentyl)-4-carboxycyclohexyl group, a 3-(4-hydroxypentyl)cyclohexyl group, a 4-(4-hydroxypentyl)cyclohexyl group, a 3-(4-hydroxypentyl)-4-carboxycyclohexyl group, a 4-(4-hydroxypentyl)-4-carboxycyclohexyl group, a 3-(5-hydroxypentyl)-4-carboxycyclohexyl group, a 4-(5-hydroxypentyl)-4-carboxycyclohexyl group, a 3-sulfocyclohexyl group, a 4-sulfocyclohexyl group, a 2,4-sulfocyclohexyl group, a 2,4-sulfocyclohexyl group, a 3,4-disulfocyclohexyl group, a 2-sulfo-4-carboxycyclohexyl group, a 3-sulfo-4-carboxycyclohexyl group, a 3,5-disulfo-4-carboxycyclohexyl group, a 2-sulfo-4-carboxymethylcyclohexyl group, a 3-sulfo-4-carboxymethylcyclohexyl group, a 3,5-disulfo-4-carboxymethylcyclohexyl group, a 2-sulfo-4-carboxyethylcyclohexyl group, a 3-sulfo-4-carboxyethyl cyclohexyl group, a 3,5-disulfo-4-carboxyethyl cyclohexyl group, a 2-sulfo-4-carboxypentylcyclohexyl group, a 3-sulfo-4-carboxypentylcyclohexyl group, and a 3,5-disulfo-4-carboxypentylcyclohexyl group, or a salt thereof. As the salt, a sodium salt or a potassium salt is preferable, and a sodium salt is more preferable, but the salt is not limited thereto. Further, the group on the cyclohexyl ring may be bonded to the axial position or to the equatorial position when the 1,1-diphenylthiosemicarbazide group is bonded to the equatorial position. That is, these groups may coordinate to cis (cis-) or to trans (trans-) with the 1,1-diphenylthiosemicarbazide group on the cyclohexyl ring.

A preferred embodiment of the thiosemicarbazide derivative of the present invention is 1,1-diphenyl-4-cyclohexyl-thiosemicarbazide represented by the chemical formula (20), wherein $R_1$ in the chemical formula (19) is a cyclohexyl group. In the present invention, the compound represented by the chemical formula (20) is particularly referred to as C8.

[Chem. 20]

(XX)

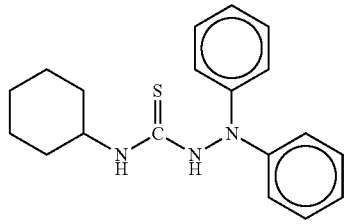

A further preferred embodiment of the thiosemicarbazide derivative of the present invention is represented by the chemical formula (6), in which $R_3$ and $R_4$ each independently represent any group or atom selected from the group consisting of a carboxyl group, a carboxymethyl group, a carboxypentyl group, a hydroxy group, an acetyl group and a hydrogen atom or a salt thereof. $R_3$ may be bonded to the axial position or to the equatorial position in the cyclohexyl ring. That is, $R_3$ may coordinate to cis (cis-) or to trans (trans-) with the 1,1-diphenylthiosemicarbazide group on the cyclohexyl ring.

[Chem. 6]

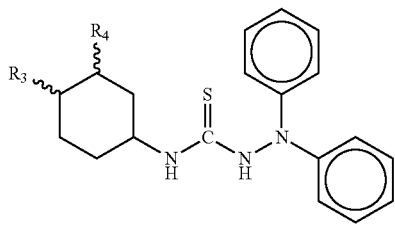

(VI)

A further preferred embodiment of the semicarbazide derivative of the present invention is represented by the chemical formula (9), in which $R_3$ represents any group selected from the group consisting of carboxyl group, carboxymethyl group, carboxypentyl group, hydroxy group and acetyl group or a salt thereof. $R_3$ may be bonded to the axial position or to the equatorial position in the cyclohexyl ring. That is, $R_3$ may coordinate to cis (cis-) or to trans (trans-) with the 1,1-diphenylthiosemicarbazide group on the cyclohexyl ring.

[Chem. 9]

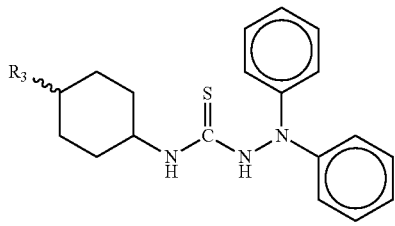

(IX)

As a further preferred embodiment of the thiosemicarbazide derivative of the present invention, 1,1-diphenyl-4-(4-carboxy (4-carboxycyclohexyl)-thiosemicarbazide. In this, the carboxy group may be bonded to the axial position in the cyclohexyl ring or to the equatorial position. That is, the carboxy group may be coordinated with 1,1-diphenylthiosemicarbazide group in the cyclohexyl ring to trans (trans-) or cis (cis-), but is preferably coordinated to cis (cis-) axis as represented by the chemical formula (13). In the present invention, the compound represented by the chemical formula (13) is particularly referred to as DSC 108, and its sodium salt is referred to as DSC 108-Na.

[Chem. 11]

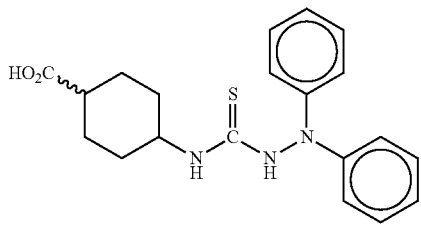

(XI)

[Chem. 13]

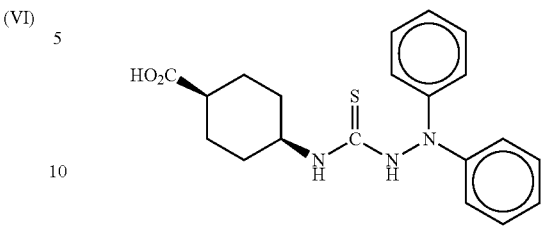

(XIII)

In the thiosemicarbazide derivatives represented by the chemical formulas (11), (13), (19) and (20), the hydrogen atom of the phenyl group in the 1,1-diphenylthiosemicarbazide group can be substituted with a functional group. The chemical formula (24) is such a derivatives as one of hydrogen atom of each of two phenyl groups in the 1,1-diphenylthiosemicarbazide group is substituted. X and Y in the formula, respectively, represent a functional group (substituent) independent from each other. In chemical formula (23), however, only one of X and Y may be substituted with a functional group, and both of X and Y may be substituted with a functional group.

[Chem. 24]

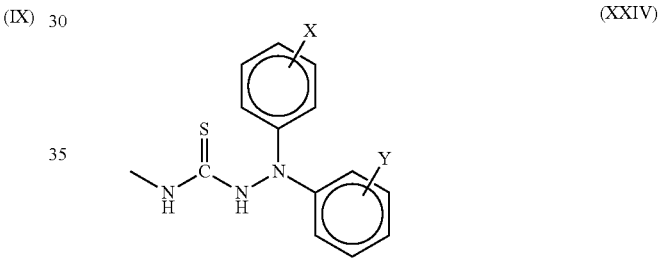

(XXIV)

Preferable examples of the functional group represented by X and Y in the chemical formula (23) include a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl group, a 2,2-dicarboxyethyl group, a 2,3-dicarboxypropyl group, a 1,2-dicarboxypropyl group, a 1,2,3-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl Group, a 1,3-dicarboxyhexyl group, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl group, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxy group, a hydroxymethyl group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a 1,2-dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl group, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxypentyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 4-sulfobutyl group, a 1-sulfopentyl group, 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group, or a salt thereof. The salt is not particularly limited, but a sodium salt or a potassium salt is preferable, and a sodium salt is particularly preferable.

Another preferred embodiment of the 1,1-diphenylsemicarbazide or 1,1-diphenylthiosemicarbazide derivative of the present invention is represented by the chemical formula (21). In the chemical formula (21), n represents an alkyl chain length, and is preferably an integer of 1 to 8, more preferably an integer of 1 to 6, and still more preferably an integer of 2 to 4. $R_6$ represents a sulfur atom or an oxygen atom, but particularly a sulfur atom.

[Chem. 21]

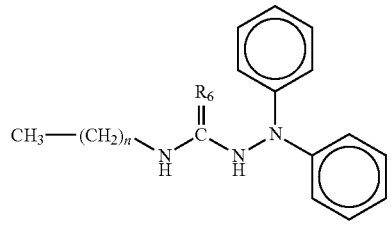

(XXI)

Another preferred embodiment of the 1,1-diphenylsemicarbazide or 1,1-diphenylthiosemicarbazide derivative of the present invention is represented by the chemical formula (22). In the chemical formula (22), $R_6$ represents a sulfur atom or an oxygen atom, particularly a sulfur atom.

[Chem. 22]

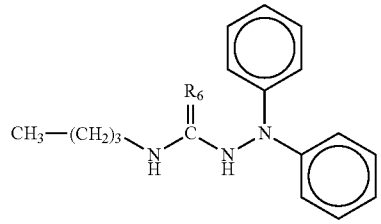

(XXII)

In the 1,1-diphenylsemicarbazide or 1,1-diphenylthiosemicarbazide derivative represented by the chemical formulas (21) and (22), the hydrogen of the phenyl group in the 1,1-diphenylsemicarbazide group or the 1,1-diphenylthiosemicarbazide group may be substituted with functional groups. In chemical formula (25) one hydrogen atom in each of two phenyl groups are substituted, in which each of X and Y represents independently a functional group (a substituent). In chemical formula (25), however, only one of X and Y may be substituted with a functional group, or of both X and Y may be substituted with a functional group.

[Chem. 25]

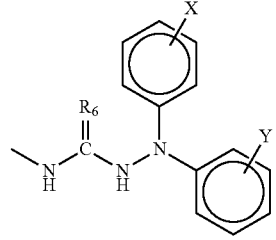

(XXV)

Suitable functional groups represented by X and Y in the chemical formula (25) include a carboxyl group, a carboxymethyl group, a 1-carboxyethyl group, a 2-carboxyethyl group, a 1-carboxypropyl group, a 2-carboxypropyl group, a 3-carboxypropyl group, a 1-carboxybutyl group, a 2-carboxybutyl group, a 3-carboxybutyl group, a 4-carboxybutyl group, 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group, a 6-carboxyhexyl group, a dicarboxymethyl group, a 1,2-dicarboxyethyl group, a 2,2-dicarboxyethyl group, a 2,3-dicarboxypropyl group, a 1,2-dicarboxypropyl group, a 3,3-dicarboxypropyl group, a 1,2-dicarboxybutyl group, a 2,3-dicarboxybutyl group, a 3,4-dicarboxybutyl group, a 2,4-dicarboxybutyl group, a 1,2-dicarboxypentyl group, a 2,3-dicarboxypentyl group, a 2,4-dicarboxypentyl group, a 2,5-dicarboxypentyl group, a 4,5-dicarboxypentyl group, a 1,2-dicarboxyhexyl group, a 1,3-dicarboxyhexyl group, a 2,3-dicarboxyhexyl group, a 2,4-dicarboxyhexyl group, a 2,5-dicarboxyhexyl group, a 2,6-dicarboxyhexyl group, a 3,5-dicarboxyhexyl group, a 3,6-dicarboxyhexyl group, a 1,2,2-tricarboxybutyl group, a 1,2,4-tricarboxybutyl group, a 2,3,4-tricarboxybutyl group, a 3,4,4-tricarboxybutyl group, a 1,2,2-tricarboxypentyl group, a 1,2,3-tricarboxypentyl group, a 2,3,4-tricarboxypentyl group, a 3,4,5-tricarboxypentyl group, a 3,5,5-tricarboxypentyl group, a 1,2,3-tricarboxyhexyl group, a 1,2,4-tricarboxyhexyl group, a 2,3,4-tricarboxyhexyl group, a 2,3,5-tricarboxyhexyl group, a 2,3,6-tricarboxyhexyl group, a 3,4,5-tricarboxyhexyl, a 3,4,6-tricarboxyhexyl group, a 4,5,6-tricarboxyhexyl group, a 1,2,3,3-tetracarboxypentyl group, a 2,3,4,5-tetracarboxypentyl group, a 2,4,5,5-tetracarboxypentyl group, a 3,4,5,5-tetracarboxypentyl group, a 1,2,3,3,5-pentacarboxyhexyl group, a 1,2,3,4,5-pentacarboxyhexyl group, a 2,3,4,5,5-pentacarboxyhexyl group, a 3,4,4,5,5-pentacarboxyhexyl group, a 1,2,4,5,5-pentacarboxyhexyl group, a hydroxyl group, a hydroxymethyl group, a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group, a 6-hydroxyhexyl group, a dihydroxypropyl group, a dihydroxybutyl group, a dihydroxypentyl group, a dihydroxyhexyl group, a trihydroxybutyl group, a trihydroxypentyl group, a trihydroxyhexyl group, a tetrahydroxypentyl group, a tetrahydroxyhexyl group, a pentahydroxyhexyl group, a hydroxycarboxymethyl group, a 1-hydroxy-2-carboxyethyl group, a 2-hydroxy-1-carboxyethyl group, a 1-hydroxy-2-carboxypropyl group, a 1,2-dihydroxy-2-carboxypropyl group, a 1,2-dihydroxy-3-carboxypropyl group, a 4-hydroxy-1-carboxybutyl group, a 1,2-dihydroxy-2-carboxybutyl group, a dihydroxy-3-carboxybutyl group, a 1,2,3-trihydroxy-4-carboxybutyl group, a 4-hydroxy-1-carboxypentyl group, a 5-hydroxy-2-carboxypentyl group, a 1,2-dihydroxy-3-carboxypentyl group, a 1,2-dihydroxy-4-carboxypentyl, a 1,2,2-trihydroxy-5-carboxypentyl group, a 5-hydroxy-1-carboxyhexyl group, a 1,2-dihydroxy-2-carboxyhexyl group, a 1,2-dihydroxy-3-carboxyhexyl group, a 1,2,2-trihydroxy-4-carboxyhexyl group, a 1,2,2-trihydroxy-5-carboxyhexyl group, a 2,3-dihydroxy-6-carboxyhexyl group, a 1-hydroxy-2,3-dicarboxypropyl group, a 2-hydroxy-3,4-dicarboxybutyl group, a 2,3-dihydroxy-3,5-dicarboxybutyl group, a 1,2,3-trihydroxy-5,6-dicarboxyhexyl group, a 2-hydroxy-3,4,4-tricarboxybutyl group, a 2,3-hydroxy-2,3,5-tricarboxypentyl group, a 5-hydroxy-2,3,6-tricarboxyhexyl group, a 5-hydroxy-2,3,4,4-tetracarboxypentyl group, a 2-hydroxy-2,4,6,6-tetracarboxyhexyl group, a 2,3-dihydroxy-2,3,4,5,6-pentacarboxyhexyl group, a sulfo group, a sulfomethyl group, a 1-sulfoethyl group, a 2-sulfoethyl group, a 1-sulfopropyl group, a 2-sulfopropyl group, a 3-sulfopropyl group, a 1-sulfobutyl group, a 2-sulfobutyl group, a 3-sulfobutyl group, a 1-sulfopentyl group, a 2-sulfopentyl group, a 3-sulfopentyl group, a 4-sulfopentyl group, a 5-sulfopentyl group, a 1-sulfohexyl group, a 2-sulfohexyl group, a 3-sulfohexyl group, a 4-sulfohexyl group, a 5-sulfohexyl group, a 6-sulfohexyl group, a disulfopropyl group, a disulfobutyl group, a disulfopentyl group, a disulfohexyl group, a trisulfobutyl group, a trisulfopentyl group, a trisulfohexyl group, a tetrasulfopentyl group, a tetrasulfohexyl group, a pentasulfohexyl group, and an acetyl group, or a salt thereof. The salt is not particularly limited, but a sodium salt or a potassium salt is preferable, and a sodium salt is particularly preferable.

The compounds of the present invention can be easily synthesized by those skilled in the art by combining well-known chemical synthesis methods, and synthesis thereof is not particularly difficult. For example, DSC108 which is a compound represented by the chemical formula (13) and its sodium salt are synthesized by the method outlined in the examples using cis-4-aminocyclohexanecarboxylic acid and 1,1-diphenylhydrazine as raw materials.

The semicarbazide derivative and the thiosemicarbazide derivative of the present invention have a function of promoting insulin secretion from pancreatic β cells. At least a part of this function is exerted through SUR1 which is a subunit constituting the $K_{ATP}$ channel expressed on the cell membrane of pancreatic β cells. That is, these compounds bind to SUR1, thereby closing the $K_{ATP}$ channel, which causes the depolarization of the pancreatic β-cell membrane, the opening of the voltage-dependent calcium channels (VDCCs), influx of calcium ions, increase of calcium ion concentration in pancreatic β cells, and induction of insulin secretion. As glucose concentration in blood is lowered by the induction of insulin secretion, the semicarbazide derivative and the thiosemicarbazide derivative of the present invention can be used as a hypoglycemic agent, particularly as a therapeutic agent for type 2 diabetic patients.

The compound of the present invention exerts its function as a hypoglycemic agent by oral administration. Therefore, they may be provided to medical institutions as tablets or powders. The semicarbazide derivative and the thiosemicarbazide derivative of the present invention have a short half-life in the blood as compared with gliclazide which is an oral hypoglycemic agent of the sulfonylurea type. Therefore, side effects such as persistent hypoglycemia and the like recognized in conventional sulfonylurea drugs should be diminished. Therefore, it is particularly effective as a therapeutic agent for patients who are not acceptable for the administration of sulfonylurea drugs due to the appearance of side effects such as persistent hypoglycemia. When the compound of the present invention is administered orally, the dose is adjusted, as need, to 1 to 100 mg/kg body weight, 10 to 100 mg/kg body weight, 1 to 30 mg/kg body weight, 10 to 30 mg/kg body weight and so on, depending on the symptoms of the patient.

Hereinafter, the method of using it as a hypoglycemic agent will be described in detail by taking DSC108 represented by the chemical formula (13) as an example of the compound of the present invention. Since the DSC108 quickly transfers to the blood by oral administration, it is supplied as a tablet or powder suitable for oral administration. However, the formulation is not limited to these. By orally administering to a patient with type 2 diabetes after meals, DSC108 can exert the function of lowering the blood glucose level of type 2 diabetic patients. Therefore, it is preferable that the DSC108 is taken after each meal. The dosage of DSC108 is adjusted, as needed, to 1 to 100 mg/kg body weight, 10 to 100 mg/kg body weight, 1 to 30 mg/kg body weight, 10 to 30 mg/kg body weight, and son on, depending on the patient's symptoms.

EXAMPLES

While the present invention will be described in further detail below referring to examples, it is not intended that the present invention be limited to the examples.

[Example 1] Insulin Secretion Stimulation Test Using MIN6-K8 Cells

MIN6-K8 cells (cells similar to the MIN6-m9 cell line deposited as FERM P-18081) were cultured in Dulbecco's modified Eagle's medium (DMEM medium) supplemented with 10% FBS, 50 μM 2-mercaptoethanol, 100 mg/L streptomycin and 60.5 mg/L penicillin sulfate at 37° C. After washing the MIN 6-K8 cells twice with medium, the cells were washed twice with 133.4 mM NaCl, 4.7 mM KCl, 1.2 mM $KH_2PO_4$, 1.2 mM $MgSO_4$, 2.5 mM $CaCl_2$, 5.0 mM $NaHCO_3$, 2.8 mM glucose, 0.1% BSA and 10 mM HEPES buffer (pH 7.4) for 30 minutes. Cells were then cultured for 30 minutes in the KRBH buffer containing the test compound and 11.2 mM glucose. After incubation, the concentration of insulin contained in the KRBH buffer solution was measured using an insulin assay kit (CIS Bio International Inc.). The concentration of insulin was obtained as a relative value when the concentration of insulin when the test compound was not added was taken as 1. Here, DSC108 and C8 were used as test compounds, and the abilities to promote insulin secretion of both drugs were compared within a concentration range of 1 μM to 100 μM. Measurement was carried out with n=3.

[Example 2] Insulin Secretion Stimulation Test Using Mice

Insulin secretion stimulation test using mouse was performed in accordance with the method described in Bonnevie-Nielsen V. Diabetes. 30. 424-9 (1981) and Miki T. Diabetes. 54. 1056-63 (2005). Male mice, 16 to 20 weeks old, fasted for 6 hours, were anesthetized by administering sodium pentobarbital at a dose of 80 mg/kg body weight. The anesthetized mouse pancreases were perfused with KRBH buffer containing 4.6% dextran and 0.25% BSA aerated at 95% $O_2$/5% $CO_2$.

Subsequently, mouse pancreases were perfused with KRBH buffer containing 2.8 mM glucose and 10 μM DSC 108, and the perfused solution was collected every minute, and the concentration of insulin contained in the perfusion solution was measured with an insulin assay kit (CIS Bio international Inc.) over time. IN parallel, as a control, mouse pancreases were perfused with a KRBH buffer solution containing 2.8 mM glucose, and the concentration of insulin contained in the perfusion solution was measured in the same manner.

[Example 3] Measurement of Intracellular Calcium Ion Concentration

In accordance with the method described in "Shimaoto K. Mol Pharmacol. 53, 195-201 (1998)", measurement of intracellular calcium concentration was performed using fura-2-acetoxymethyl ester (Fura-2-AM, Dojindo Inc.) which is a calcium ion sensitive fluorescent reagent. MIN6-K8 cells were grown in Dulbecco's modified Eagle medium (DMEM medium) supplemented with 10% FBS, 50 μM 2-mercaptoethanol, 100 mg/L streptomycin and 60.5 mg/L penicillin sulfate in a humidified condition of 5% CO, at 37° C. MIN6-K8 cells were then left alone in KRBH buffer containing 5 μM Fura-2-AM and 2.8 mM glucose at 37° C. for 20 minutes. Then, KRBH buffer containing 3 μM, 10 μM or 30 μM of DSC108 was each added as a test compound and fluorescence intensity at 340 nm and 380 nm were measured using a dual wavelength fluorometer (Fluoroskan Ascent CF, Labsystem Inc.) over time for 20 minutes and the values of "fluorescence intensity at 340 nm/fluorescence intensity at 380 nm" were determined. This value shows a positive correlation with calcium ions flowing into the cell. Measurement was carried out with n=4.

[Example 4] [$^3$H] Glibenclamide Competition Test

An expression vector incorporating a gene encoding human SUR1 (hSUR1) was introduced into MIN6-K8 cells by a conventional method to establish a cell line MIN6-K8, which expresses hSUR1 strongly. The MIN6-K8 cells expressing strongly hSUR1 were cultured in a buffer containing 10 nM [$^3$H] glibenclamide and DSC108-Na for 30 minutes. In this, the concentration of DSC108-Na in the buffer was 300 μM to 1 mM. The cells were vacuum-filtered and recovered on Whatmann GF/C filters (Whatmann International Inc.), and then the filters were washed three times with 4 mL of ice-cold buffer. After washing, radioactivities of the filters were measured with a liquid scintillation counter, and the amount of [$^3$H] glibenclamide bound to MIN6-K8 cells expressing strongly hSUR1 via hSUR1 was measured. Then, the value at the time of non-addition of DSC108-Na was taken as 100%, and the binding amount (%) of [$^3$H] glibenclamide to MIN6-K8 cells was determined as a relative value to this value.

[Example 5] Electrophysiological Test Using Pancreatic β Cells

Islets were isolated from C57BL/6 mice by collagenase digestion method in accordance with the method described "in Shibasaki T. Proc Natl Acad Sci USA. 104, 19333-8 (2007)". The pancreatic islet cells were dispersed and cultured in DMEM supplemented with 10% FBS, and then plated on a 3.5 cm dish sheeted prior to the experiment with a glass flake coated with collagen.

Membrane potential of pancreatic β cells was measured by a perforated patch clamp method (Gonoi T J J. Biol. Chem., 269: 16989-92 (1994)) in current clamp mode. As an extracellular solution, 5 mM HEPES buffer-NaOH (pH 7.4) containing 143 mM NaCl, 5.4 mM KCl, 1.8 mM $CaCl_2$, 0.5 mM $MgCl_2$, 0.33 mM $NaHPO_4$ and 5.5 mM glucose was used. As a pipette solution, 11 mM HEPES-KOH buffer (pH 7.4) containing 107 mM KCl, 11 mM EGTA, 2 mM $MgSO_4$, 1 mM $CaCl_2$ and 1 μM ATP-$K_2$ was used. Under this condition, outward current induced by 30 μM DSC108 was measured by a pierced patch clamp assay.

[Example 6] Electrophysiological Test Using $K_{ATP}$ Channel Expressing COS-1 Cells Expression vectors incorporating the gene encoding human SUR1 (hSUR1) and expression vector incorporating the gene encoding human Kir6.2 (hKir6.2) were introduced into COS-1 cells together, and the $K_{ATP}$ channel was reconstituted with COS-1 cells (Inagaki N. Science. 270, 1166-70 (1995)). The cells were cultured in DMEM medium (Sigma-Aldrich Inc.) supplemented with 10% FBS and plated on a 3.5 cm dish on which glass flakes coated with collagen had been spread prior to the experiment, and incubated at 37° C. for 24 to 72 hours.

The membrane potential of COS-1 cells reconstituted with $K_{ATP}$ channels was determined by the method described in (Gonoi TJ Biol. Chem., 269: 16989-92 (1994)), in the current clamp mode with perforated patch clamp method. As an extracellular solution, 5 mM HEPES buffer-NaOH (pH 7.4) containing 143 mM NaCl, 5.4 mM KCl, 1.8 mM $CaCl_2$, 0.5 mM $MgCl_2$, 0.33 mM $NaHPO_4$ and 5.5 mM glucose was used. Inhibitory effect of DSC108 on the polarization of COS-1 cell membrane via $K_{ATP}$ channel induced by 300 μM diazoxide (Sigma Chemical Inc.) under these conditions was measured.

At this time, outward current induced by 300 μM diazoxide (Sigma Chemical Inc.) was measured by whole cell patch clamp assay, and this value was set to 0 mV. The value of outward current when DSC108, glibenclamide or glicrazaide (Sigma Chemical Inc.) was added together with diazoxide was determined to determine the inhibitory effect ($IC_{50}$) of these agents on the polarization of the cell membrane induced by diazoxide.

[Example 7] Measurement of Blood Concentration of DSC108

To male C57BL/6JJc1 mice of 18 to 28 weeks of age (CLEA Japan Inc.), DSC108Na and gliclazide as a test compound were orally administered at a dose of 30 mg/kg body weight. Peripheral blood was collected over time from the tail vein after administration. The collected blood was centrifuged to obtain plasma. An extraction solution (chloroform:methanol:water=1:2:0.8) containing 20 μM methionine sulfone was added to the plasma, followed by stirring and centrifugation. After filtering the extracted solution fraction with a 5 kD filter (Millipore Inc.), the extract was lyophilized. The extract obtained by lyophilization was dissolved in pure water and subjected to mass spectrometry. Mass spectrometry was performed using a mass spectrometer (LCMS-8050, Shimazu Inc.) fitted with liquid chromatography (Nexera UHPLC, Shimazu Inc.). Separation by liquid chromatography was performed with a double gradient of 0.1% formic acid aqueous solution and 0.1% acetonitrile formic acid solution using Discovery HS F5 column (3 μm, 2.1 mm×150 mm, Shigma-Aldrich Inc.).

[Example 8] Measurement of Hypoglycemic Action Using Wild Type Mice

To male C57BL/6JJc1 mice (CLEA Japan Inc.) of 18 to 30 weeks old fasted for 16 hours, 10, 30 or 100 mg/kg body weight of DSC108-Na was orally administered 20 minutes before glucose loading (1.5 g glucose/kg body weight) (10 mg/kg body weight administration group, 30 mg/kg body weight administration group and 100 mg/kg body weight administration group, respectively). As a control, DSC108-Na non-administration group (vehicle administration group) was placed. Glucose concentration in the blood was measured over time over 120 minutes after the administration using Antsense III glucose analyzer (Horiba Inc.). Measurement was carried out using 4 mice in each group.

[Example 9] Measurement of Hypoglycemic Action Using Type 2 Diabetes Model Rats

To male GK/Slc rats (Japan SLC Inc.) 18-30 weeks old fasted for 6 hours, DSC108-Na was orally administered at 100 mg/kg body weight 20 minutes before glucose loading (1.5 g glucose/kg body weight) (DSC108-Na administration group). As a control, DSC108-Na non-administration group (vehicle administration group) was placed. The glucose concentration in the blood was measured using Antsense III glucose analyzer (Horiba Inc.). In addition, blood insulin concentration was measured by an ELISA method using an insulin measurement kit (Morinaga Inc.). Not limited to this examination, all animal tests were conducted in accordance with the provisions of the Kobe University Animal Experiment Implementation Rules with the approval of the Animal Experimental Ethics Committee of Kobe University.

[Example 10] Insulin Secretion Stimulation Test of Derivatives of Various 1,1-diphenyl-4-cyclohexyl-semicarbazide Using MIN6-K8 Cells For the 1,1-diphenyl-4-cyclohexyl-semicarbazide derivatives numbered 2 to 7 shown in Table 1, an insulin secretion stimulation test using the above MIN6-K8 cells was performed. The concentration of the test compound was 100 μM, and the amount of secretion when the amount of insulin secreted when no test compound was added was taken as 1 was measured. Incidentally, the number 1 is 1,1-diphenyl-4-cyclohexyl-semicarbazide represented by the chemical formula (18). Numbers 2 to 7 are compounds in which one of hydrogen atoms on the cyclohexyl ring of 1,1-diphenyl-4-cyclohexyl-semicarbazide is substituted with a carboxyl group.

TABLE 1

Chemical formulas of derivatives of 1,1-diphenyl-4-cyclohexyl-3-semicarbazide

| No. | 1 | 2 | 3 | 4 |
|---|---|---|---|---|

TABLE 1-continued

| No. | 5 | 6 | 7 |
|---|---|---|---|
| | HO₂C-cyclohexyl-R (stereo) | cyclohexyl with CO₂H and R | cyclohexyl with CO₂H and R (different stereo) |

R denotes the following formula:

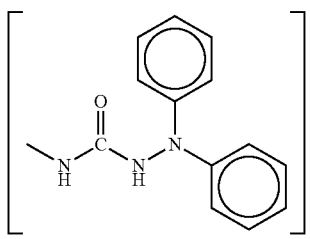

[Example 11] Experimental Results: Insulin Secretion Stimulation Test Using MIN6-K8 Cells The results of the insulin secretion stimulation test using MIN6-K8 cells are shown in FIG. 1. Both DSC108 and C8 promoted insulin secretion from MIN6-K8 cells in a concentration-dependent manner. However, at concentrations of 1 μM to 30 μM both insulin promoted insulin secretion in a dose-dependent manner, but at a concentration of 100 μM, the amount of insulin secretion from MIN6-K8 cells decreased as compared with the concentration at 30 μM did. In addition, in the range of 1 μM to 100 μM concentration, DSC108 showed higher insulin secretion promoting ability as compared with C8. These results indicate that C8 and DSC108 are both promising as a therapeutic agent for diabetes which exerts insulin secretion promoting ability in vivo. In addition, DSC108 has a higher ability to promote insulin secretion as compared with C8, indicating that it is more promising as a therapeutic agent for diabetes.

[Example 12] Experimental Results: Insulin Secretion Stimulation Test Using Mice The results of the insulin secretion stimulation test using mice are shown in FIG. 2. The concentration of insulin contained in the perfusion liquid increased 5 minutes after the initiation of perfusion with KRBH buffer containing 10 μM DSC108. This rise in insulin concentration was temporary, and the concentration of insulin returned to baseline 9 minutes after the start of perfusion. This result indicates that the insulin secretion stimulating effect of DSC108 disappears promptly after administration. When the insulin secretion stimulating effect of the drug is maintained in vivo, adverse reactions such as hypoglycemia may occur, and β cell may be exhausted by persistent stimulation, and the symptoms of diabetes may worsen is there. As shown in FIG. 2, since the effect of DSC108 disappears rapidly after administration, it is considered that there is little possibility that side effects such as hypoglycemia occur by DSC108 administration.

[Example 13] Experimental Results: Measurement of Intracellular Calcium Ion Concentration The measurement results of intracellular calcium ion concentration are shown in FIG. 3. DSC108 increased intracellular calcium ion concentration in a concentration-dependent manner within the concentration range of 3 μM to 30 μM. These results indicate that the induction of insulin secretion by DSC108 occurs via increased elevation of calcium ion concentration in pancreatic β cells.

[Example 14] Experimental Result: [$^3$H] Glibenclamide Competition Test

The measurement results of intracellular calcium ion concentration are shown in FIG. 4. DSC108 inhibited the binding of [$^3$H] glibenclamide to hSUR1-strongly expressed MIN6-K8 cells in a concentration-dependent manner. This result indicates that DSC108 competes with [$^3$H] glibenclamide and binds to hSUR1, indicating that DSC108 also binds to hSUR1.

[Example 15] Experimental Results: Electrophysiological Test Using Pancreatic β Cells The membrane potential of pancreatic β cells was −69±2 mV in the absence of DSC108. On the other hand, the membrane potential of pancreatic β cells was −54±4 mV in the presence of 30 μM DSC108. This result shows that DSC108 has the function of inducing depolarization of pancreatic β cells.

[Example 16] Experimental Results: Electrophysiological Test Using $K_{ATP}$ Channel Expressing COS-1 Cells DSC108 inhibited polarization of COS-1 cell membrane via $K_{ATP}$ channel induced by diazoxide in a concentration-dependent manner with an $IC_{50}$ of 2.3 μM. Together with the results of electrophysiological tests using pancreatic β cells, this result indicates DSC108 induces insulin secretion by binding to SUR1, closing the $K_{ATP}$ channel, inducing cell membrane depolarization, and elevating the calcium ion concentration in β cells.

[Example 17] Experimental Result: Measurement of Blood Concentration of DSC108

The results of blood concentration measurement of the DSC108 are shown in FIG. 5. DSC108 orally administered as DSC108-Na showed the highest value of 72.4 μM in blood concentration 30 min after administration and then quickly disappeared from the blood. On the other hand, Glyclazide, an oral hypoglycemic agent of the sulfonylurea series, showed the highest blood concentration of approximately 100 μM at 60 minutes after administration, and the blood concentration remained as high as 75 µM even after 120 minutes. It is thought that sulfonylureas such as gliclazide cause persistent hypoglycemia, which is caused by the fact that they are stable in vivo. Since DSC108 quickly disappears from the blood as compared with gliclazide, it can be expected that side effects such as persistent hypoglycemia and the like are reduced when it is used as an oral hypoglycemic agent.

[Example 18] Experimental Results: Measurement of Hypoglycemic Action Using Wild Type Mice The measurement results of the hypoglycemic effect using wild type mice are shown in FIG. 6. DSC108 orally administered as DSC108-Na showed a dose-dependent hypoglycemic effect in the dose range of 10 to 100 mg/kg body weight.

[Example 19] Experimental Results: Measurement of Hypoglycemic Action Using Type 2 Diabetes Model Rats The measurement results of the hypoglycemic effect using type 2 diabetes model rats are shown in FIGS. 7 and 8. The GK/Slc rats used here are non-obese type 2 diabetes model rats showing insulin secretion failure accompanied by pancreatic β cell glucose metabolism abnormality. By orally administering DSC108-Na at a dose of 100 mg/kg body weight to GK/Slc rats, an increase in blood levels of insulin was observed 20 minutes after administration (FIG. 7). In addition, when DSC108-Na was orally administered to GK/Slc rats at a dose of 100 mg/kg body weight, the effect of lowering the glucose concentration in the blood continued for 120 minutes after administration (FIG. 8).

[Example 20] Experimental Results: Insulin Secretion Stimulation Test of Derivatives of Various 1,1-diphenyl-4-cyclohexyl-semicarbazide Using MIN6-K8 Cells Insulin secretion was promoted with 1,1-diphenyl-4-cyclohexyl-semicarbazide number 1 and derivatives of numbers 2 to 5 shown in Table 1 (FIG. 9). However, insulin secretion promoted by the derivative of number 4 was insignificant. On the other hand, insulin secretion was suppressed in the derivatives numbered 6 and 7. The 1,1-diphenyl-4-cyclohexyl-semicarbazide derivatives numbered 2 and 3, in which a carboxyl group was introduced at the 4-position of the cyclohexyl ring, exhibited a high insulin secretion-promoting ability and the derivative numbered 2 in which the carboxyl group was substituted as cis-showed the highest ability to promote insulin secretion.

[Example 21] Experimental Result: Summary

Based on the above results, DSC108 and its sodium salt, which are thiosemicarbazide derivatives, have a hypoglycemic action and quickly disappear in blood as compared with gliclazide which is an oral hypoglycemic agent of the sulfonylurea series. Therefore, it can be used as an agent for treating type 2 diabetes as an oral hypoglycemic agent with reduced side effects such as persistent hypoglycemia observed in sulfonylurea drugs.

[Example 22] Synthesis of DSC108

DSC108 and its sodium salt can be synthesized by the method outlined in FIG. 10 using cis-4-aminocyclohexanecarboxylic acid and 1,1-diphenylhydrazine as raw materials.

INDUSTRIAL APPLICABILITY

A new therapeutic agent can be provided to the clinical site in place of conventional therapeutic agents for type 2 diabetes, which has a low occurrence rate of side effects such as persistent hypoglycemia observed in oral hypoglycemic agents such as sulfonylurea.

The invention claimed is:

1. A compound of the formula (VII):

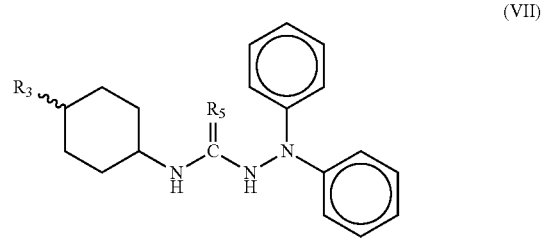

(VII)

wherein $R_3$ represents a group selected from the group consisting of a carboxyl group, a carboxymethyl group, a carboxypentyl group, a hydroxy group, and an acetyl group, or a salt thereof, $R_5$ represents an oxygen atom or a sulfur atom, and $R_3$ is coordinated to cis (cis-) or trans (trans-) with 1,1-diphenyl semicarbazide group.

2. The compound according to claim 1, represented by formula (VIII):

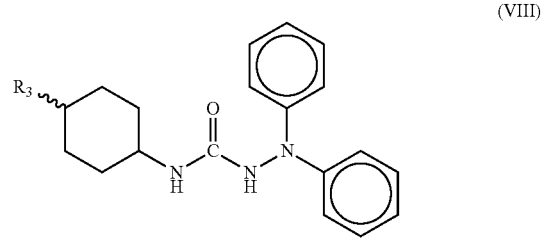

(VIII)

wherein $R_3$ represents a group selected from the group consisting of a carboxyl group, a carboxymethyl group, a carboxypentyl group, a hydroxy group, and an acetyl group, or a salt thereof, and $R_3$ is coordinated to cis (cis-) or trans (trans-) with 1,1-diphenyl semicarbazide group.

3. The compound according to claim 1, represented by formula (IX):

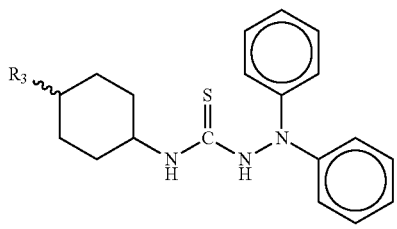

(IX)

wherein R₃ represents a group selected from the group consisting of a carboxyl group, a carboxymethyl group, a carboxypentyl group, a hydroxy group, and an acetyl group, or a salt thereof, and R₃ is coordinated to cis (cis-) or trans (trans-) with 1,1-diphenyl semicarbazide group.

4. The compound according to claim 1, wherein R₃ represents a carboxyl group or a salt thereof.

5. The compound according to claim 1, wherein the salt is a sodium salt or a potassium salt.

6. The compound according to claim 5, wherein the salt is a sodium salt.

7. The compound according to claim 2, represented by formula (X):

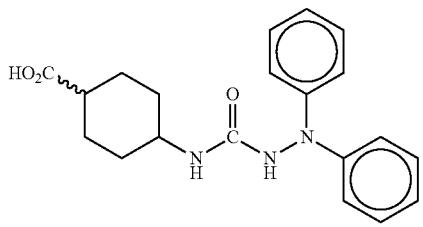

(X)

wherein the carboxyl group and the 1,1-diphenylsemicarbazide group are coordinated to cis (cis-) or trans (trans-).

8. The compound according to claim 3, represented by formula (XI):

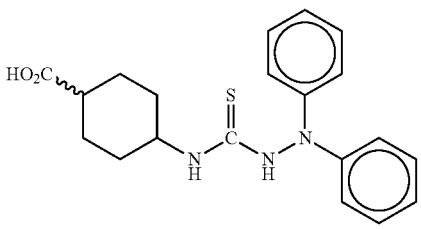

(XI)

wherein the carboxyl group and the 1,1-diphenylsemicarbazide group are coordinated to cis (cis-) or trans (trans-).

9. The compound according to claim 7, represented by formula (XII) or the salt thereof:

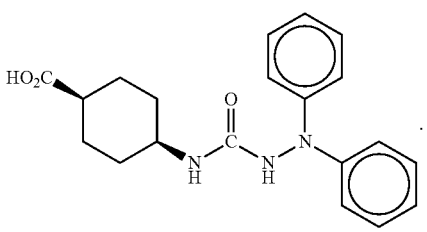

(XII)

10. The compound according to claim 8, represented by formula (XIII) or the salt thereof:

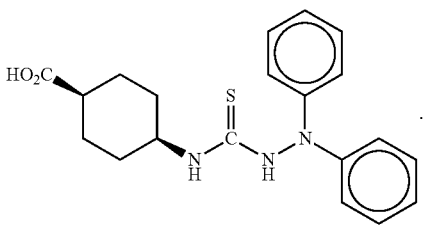

(XIII)

11. The compound according to claim 10, wherein the salt is a sodium salt or potassium salt.

12. A pharmaceutical composition comprising the compound according to claim 10 as an active ingredient.

* * * * *

UNITED STATES PATENT AND TRADEMARK OFFICE
CERTIFICATE OF CORRECTION

PATENT NO. : 10,759,749 B2
APPLICATION NO. : 16/329025
DATED : September 1, 2020
INVENTOR(S) : Susumu Seino et al.

Page 1 of 1

It is certified that error appears in the above-identified patent and that said Letters Patent is hereby corrected as shown below:

On the Title Page

Item (57), delete "nobel" and insert --novel-- therefor.

On page 2, Item (56), Line 17 should read:
K K.Ginwala, et al. Synthesis of 1, l-Diphenyl-4-Substituted Thiosemicarbazides Current Science, Letter of the Editor, XP 55670845, 1963, pp. 159-160.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*